(12) United States Patent
Nishizaki et al.

(10) Patent No.: US 9,012,500 B2
(45) Date of Patent: Apr. 21, 2015

(54) PKC-ε ACTIVATOR

(75) Inventors: Tomoyuki Nishizaki, Kobe (JP); Akito Tanaka, Toyonaka (JP)

(73) Assignee: Nishizaki Bioinformation Research Institute, Kobe-shi (JP)

( * ) Notice: Subject to any disclaimer, the term of this patent is extended or adjusted under 35 U.S.C. 154(b) by 49 days.

(21) Appl. No.: 13/885,751

(22) PCT Filed: Nov. 15, 2011

(86) PCT No.: PCT/JP2011/076302
§ 371 (c)(1),
(2), (4) Date: May 16, 2013

(87) PCT Pub. No.: WO2012/067111
PCT Pub. Date: May 24, 2012

(65) Prior Publication Data
US 2013/0331454 A1    Dec. 12, 2013

(30) Foreign Application Priority Data
Nov. 16, 2010   (JP) ................................. 2010-255967

(51) Int. Cl.
*A61K 31/235* (2006.01)
*C07C 53/132* (2006.01)

(52) U.S. Cl.
CPC ............. *C07C 53/132* (2013.01); *A61K 31/235* (2013.01); *C07B 2200/07* (2013.01)

(58) Field of Classification Search
CPC ............................ A61K 31/235; C07C 53/132
USPC .......................................... 514/542; 562/506
See application file for complete search history.

(56) References Cited

U.S. PATENT DOCUMENTS

2005/0075393 A1    4/2005   Nishizaki et al.

FOREIGN PATENT DOCUMENTS

| JP | 2004-516277 | 6/2004 |
| JP | 2008-143819 | 6/2008 |
| JP | 2010-202525 | 9/2010 |
| WO | WO 02/50013 A1 | 6/2002 |

OTHER PUBLICATIONS

International Search Report issued Feb. 21, 2012 in Application No. PCT/JP2011/076302.

Tomoyuki Nishizaki, "Linoleic acid derivative DCP-LA facilitates hippocampal synaptic transmission by targeting presynaptic α7 ACh receptors", Seitai no Kagaku, Jun. 15, 2009, vol. 60, No. 3, pp. 248-255.

Takeshi Kanno, et al., "The newly synthesized linoleic acid derivative DCP-LA selectively activates PKC-ε", Society for Neurochemistry, vol. 45, No. 2, P3-N-073, Aug. 25, 2006, p. 552.

Akito Tanaka, et al., "The Newly Synthesized Linoleic Acid Derivative FR236924 Induces a Long-Lasting Facilitation of Hippocampal Neurotransmission by Targeting Nicotinic Acetylcholine Receptors", Bioorganic and Medicinal Chemistry Letters, vol. 13, 2003, pp. 1037-1040.

Takeshi Kanno, et al., "The linoleic acid derivative DCP-LA selectively activates PKC-ε, possibly binding to the phosphatidylserine binding site", Journal of Lipid Research, vol. 47, 2006, pp. 1146-1156.

Tadashi Shimizu, et al., "α,β-DCP-LA Selectively Activates PKC-ε and Stimulates Neurotransmitter Release with the Highest Potency among 4 Diastereomers", Cellular Physiology and Biochemistry, vol. 27, 2011, pp. 149-158.

Takahiro Yaguchi, et al., "Linoleic acid derivative DCP-LA improves learning impairment in SAMP8", Neuropharmacology and Neurotoxicology, NeuroReport, vol. 17, No. 1, pp. 105-108.

Takeshi Kanno, et al., "8-[2-(2-pentyl-cyclopropylmethyl)-cyclopropyl]-octanoic acid stimulates GABA release from interneurons projecting to CA1 pyramidal neurons in the rat hippocampus via pre-synaptic α7 acetylcholine receptors", Journal of Neurochemistry, vol. 95, 2005, pp. 695-702.

Tetsu Nagata, et al., "The newly synthesized linoleic acid derivative DCP-LA ameliorates memory deficits in animal models treated with amyloid-β peptide and scopolamine", Psychogeriatrics, vol. 5, 2005, pp. 122-126.

S. Yamamoto, et al., "The Linoleic Acid Derivative FR236924 Facilitates Hippocampal Synaptic Transmission by Enhancing Activity of Presynaptic α7 Acetylcholine Receptors on the Glutamatergic Terminals", Neuroscience, vol. 130, 2005, pp. 207-213.

*Primary Examiner* — Raymond Henley, III
(74) *Attorney, Agent, or Firm* — Oblon, McClelland, Maier & Neustadt, L.L.P.

(57) ABSTRACT

The present invention aims to obtain an optical isomer of DCP-LA, which shows more superior activity and is suitable for clinical utilization, and provide an agent having a superior PKC-ε activation action, a prophylactic and/or therapeutic agent for neurotransmitter release disorders, and a prophylactic and/or therapeutic agent for neuropsychiatric diseases, which contain the isomer as an active ingredient.

A compound represented by the following formula:

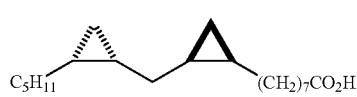

or a pharmaceutically acceptable salt thereof, and a selective PKC-ε activator containing same as an active ingredient, and is the like.

14 Claims, 10 Drawing Sheets

PKC-ε ACTIVATOR

CROSS REFERENCE TO RELATED APPLICATIONS

The present application is a 35 U.S.C. §371 national stage patent application of International patent application PCT/JP11/076302, filed on Nov. 15, 2011, the text of which is incorporated by reference, and claims the benefit of the filing dates of Japanese Application No. 2010-255967, filed on Nov. 16, 2010, the text of which is also incorporated by reference.

TECHNICAL FIELD

The present invention relates to a protein kinase C-ε (PKC-ε) activator. The present invention also relates to a prophylactic and/or therapeutic agent for neurotransmitter release disorders, and a prophylactic and/or therapeutic agent for neuropsychiatric diseases.

BACKGROUND ART

In recent years, dementia has become a major medical problem worldwide. Dementia is a disease accompanied by various kinds of symptoms centering around learning and memory disorders and impaired judgment, and the symptoms and progress thereof vary depending on the diseases causing them. However, all cases are common in that the quality of life of patients is markedly impaired. Given the fact that caregivers including the patients' families are forced to offer a large amount of labor, dementia can be said a very serious problem at the social level. Since the increasing population of elderly citizens resulting from the increasing life span is related to the increase of dementia patients, the number of dementia patients is predicted to further increase in years ahead in Japan. In addition, there are many people suffering from aging-related cognitive impairment which is not classified as dementia.

As for dementia patients, various etiologies have been reported. Reported in Alzheimer-type dementia, Lewy body dementia and the like is a decrease in the intracerebral acetylcholine concentration. Use of an acetylcholine degrading enzyme inhibitor based on this fact is the most successful method to the present for the treatment of dementia, particularly Alzheimer-type dementia. In Japan, various kinds of acetylcholine degrading enzyme inhibitors have heretofore been developed, including already commercially available donepezil hydrochloride (trade name Aricept). However, such medicaments do not fundamentally treat dementia but show an effect of delaying the progression of symptoms. As for donepezil hydrochloride, moreover, the problem of side effects such as the risk of developing acute renal failure, rhabdomyolysis and the like has been reported. For these reasons, the development of a drug for improving dementia, which is safer and shows high effect, has been desired.

The present inventors found 8-(2-(2-pentyl-cyclopropylmethyl)-cyclopropyl)-octanoic acid (DCP-LA) as a compound having a long-term enhancing action on a synaptic transmission efficiency, which enables delay of metabolism in the body and intracerebral, stable physiological activity in the body, and can induce synaptic transmission long-term enhancing phenomenon (LTP, long-term potentiation) involved in learning and memory (patent document 1). LTP is considered to be involved in the onset of, for example, various nerve and mental diseases such as Alzheimer's disease and the like. Therefore, a substance that induces LTP expression has a possibility of becoming a therapeutic or prophylactic drug for such nerve and mental diseases including dementia.

Several reports are also available regarding DCP-LA. For example, there have been reported that DCP-LA selectively and directly activates PKC-ε (non-patent document 1), DCP-LA improves cognitive dysfunction of senescence-accelerated mouse (non-patent document 2), DCP-LA increases release of γ aminobutyric acid from hippocampus nerve cells (non-patent document 3), DCP-LA improves cognitive dysfunction of amyloid β peptide- or scopolamine-treated rat (non-patent document 4), and DCP-LA promotes hippocampus synaptic transmission by using, as a target, an α7 nicotinic acetylcholine receptor that expresses at the glutamatergic presynaptic terminal (non-patent document 5). In recent years, moreover, it has been reported that DCP-LA has an action to suppress nerve cell death induced by oxidative stress (patent document 2).

DOCUMENT LIST

Patent Documents patent document 1: WO02/50013
patent document 2: JP-A-2008-143819

Non-patent Documents non-patent document 1: Kanno T et al., J Lipid Res., 2006, 47(6):1146-56.
non-patent document 2: Yaguchi T et al., Neuroreport, 2006, 23; 17(1):105-8.
non-patent document 3: Kanno T et al., J. Neurochem., 2005, 95(3):695-702.
non-patent document 4: Nagata T et al., Psychogeriatrics, 2005, 5:122-126.
non-patent document 5: Yamamoto et al., Neuroscience, 2005, 130(1):207-213.

SUMMARY OF THE INVENTION

Problems to be Solved by the Invention

In general, when a compound contained as an active ingredient of a medicament has optical isomers, the pharmacological action and in vivo kinetics may vary between the optical isomers. In this event, only one of the optically active forms is utilized with the aim of enhancing the activity of the active ingredient, decreasing the dose, or avoiding unpreferable side effects and the like. Therefore, a means of selectively and efficiently producing an optically active form is desired. For example, a method of optically resolving a racemate by liquid chromatography using an optically active column filler is known. When the object compound is a basic or acidic compound, an optical resolution method including forming a diastereomer salt by an acid-base reaction with an optically active acid or amine, and separating the salt by utilizing the difference in the properties of the salts is known.

While it is known that 8-(2-(2-pentyl-cyclopropylmethyl)-cyclopropyl)-octanoic acid (DCP-LA) has various physiological activities and is useful for the prophylaxis or treatment of various nerve and mental diseases such as Alzheimer's disease and the like, its optical isomers and a method of selectively and efficiently producing same are not known.

Therefore, the present invention aims to obtain an optical isomer of DCP-LA, which shows more superior activity and is suitable for clinical utilization, and provide an agent having a superior PKC-ε activation action, a prophylactic and/or therapeutic agent for neurotransmitter release disorders, and a prophylactic and/or therapeutic agent for neuropsychiatric diseases, which contain the isomer as an active ingredient.

Means of Solving the Problems

The present inventors have conducted intensive studies in view of the above-mentioned problem and established a method of efficiently obtaining 4 optical isomers of DCP-LA. Furthermore, they have particularly found, from among the 4 optical isomers, a superior PKC-ε activation action and a neurotransmitter release promoting action in a particular optical isomer, α,β-DCP-LA, which resulted in the completion of the present invention. These actions can afford good balance of the neural activity of the whole brain, and therefore, application of α,β-DCP-LA to various neuropsychiatric diseases (various types of dementia including Alzheimer's disease, Parkinson's disease, depression etc.) can be expected.

Accordingly, the present invention is as described below.

[1] A compound represented by the following formula:

or a pharmaceutically acceptable salt thereof.
[2] A selective PKC-ε activator containing the compound of the above-mentioned [1] or a pharmaceutically acceptable salt thereof as an active ingredient.
[3] A prophylactic and/or therapeutic agent for a neurotransmitter release disorder, containing the compound of the above-mentioned [1] or a pharmaceutically acceptable salt thereof as an active ingredient.
[4] A prophylactic and/or therapeutic agent for a neuropsychiatric disease, containing the compound of the above-mentioned [1] or a pharmaceutically acceptable salt thereof as an active ingredient.
[5] The agent of the above-mentioned [4], wherein the neuropsychiatric disease is at least one kind selected from the group consisting of an age-related cognitive decline, neurodegenerative disease, vascular dementia, viral encephalitis, alcohol-induced persisting dementia, and cognitive decline caused by other disease, Parkinson's disease, extrapyramidal disease, depression, panic syndrome, emotional disturbance syndrome, and frustrated disease.
[6] The agent of the above-mentioned [5], wherein the neurodegenerative disease is Alzheimer's disease, Parkinson's disease, diffuse Lewy body disease (dementia having Lewy body), frontotemporal dementia, Pick's disease, Creutzfeldt-Jakob disease, Huntington's disease, or progressive supranuclear palsy.
[7] The agent of the above-mentioned [5], wherein the vascular dementia is caused by multiple lacunar infarcts, Binswanger's disease, or diffuse infarction in the white matter.
[8] The agent of the above-mentioned [5], wherein the viral encephalitis is herpes encephalitis, HIV encephalitis or syphilitic encephalitis.
[9] The agent of the above-mentioned [5], wherein the alcohol-induced persisting dementia is Korsakoff's syndrome or Wernicke encephalopathy.
[10] The agent of the above-mentioned [5], wherein the cognitive decline caused by other disease is caused by normal pressure hydrocephalus, chronic subdural hematoma, moya-moya disease, dementia pugilistica, hypothyroidism, hypercalcemia, hypoglycemia, vitamin B1 deficiency, vitamin B12 deficiency, or folic acid deficiency.
[11] A prophylactic and/or therapeutic agent for insomnia, pain or gastrointestinal motility disorder, containing the compound of the above-mentioned [1] or a pharmaceutically acceptable salt thereof as an active ingredient.
[12] A method for the prophylaxis and/or treatment of a neuropsychiatric disease, comprising administering an effective amount of the compound of the above-mentioned [1] or a pharmaceutically acceptable salt thereof to a subject.
[13] A method for the prophylaxis and/or treatment of insomnia, pain or a gastrointestinal motility disorder, comprising administering an effective amount of the compound of the above-mentioned [1] or a pharmaceutically acceptable salt thereof to a subject.
[14] A compound represented by the following formula:

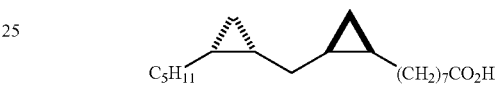

or a pharmaceutically acceptable salt thereof, which is used for the prophylaxis and/or treatment of at least one kind of a disease or pathology selected from a neuropsychiatric disease, insomnia, pain and a gastrointestinal motility disorder.

Effect of the Invention

The agent of the present invention containing α,β-DCP-LA as an active ingredient has a selective and directly strong PKC-ε activation action, and can further stimulate release of a neurotransmitter such as glutamic acid, dopamine and serotonin. Therefore, it afford good balance of the neural activity of the whole brain, and therefore, is useful for the treatment of neuropsychiatric diseases such as various types of dementia including Alzheimer's disease, Parkinson's disease, depression and the like.

DESCRIPTION OF EMBODIMENTS

Figure 1:
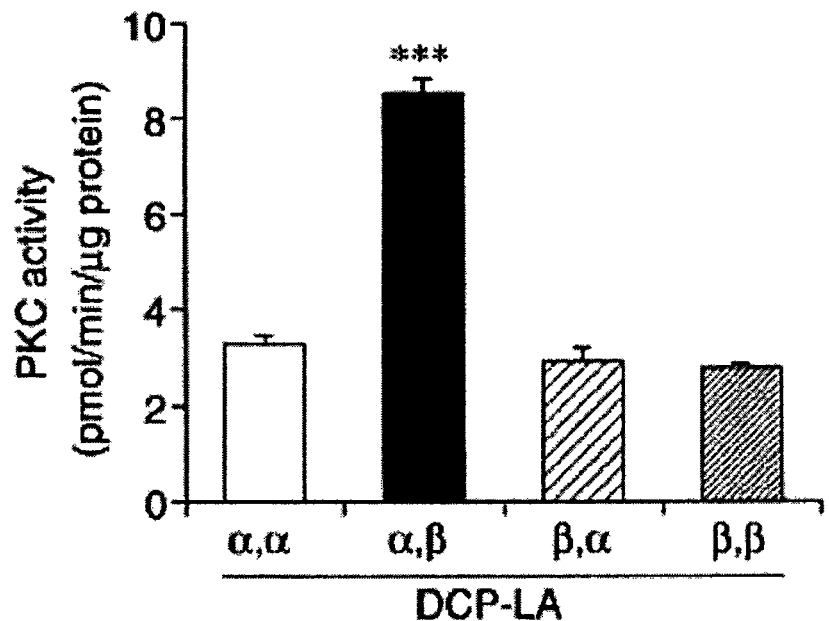
FIG. 1 is a graph showing the PKC activation action of the optical isomers (α,α-, α,β-, β,α-, β,β-) of DCP-LA on PC-12 cells. The PKC activation action of each optical isomer is shown by the average value (±SEM) (n=6). ***P<0.001 (comparison with PKC activation action induced by α,α-, β,α-, or β,β-DCP-LA); Dunnett's test

DCP-LA contains 4 optical isomers.

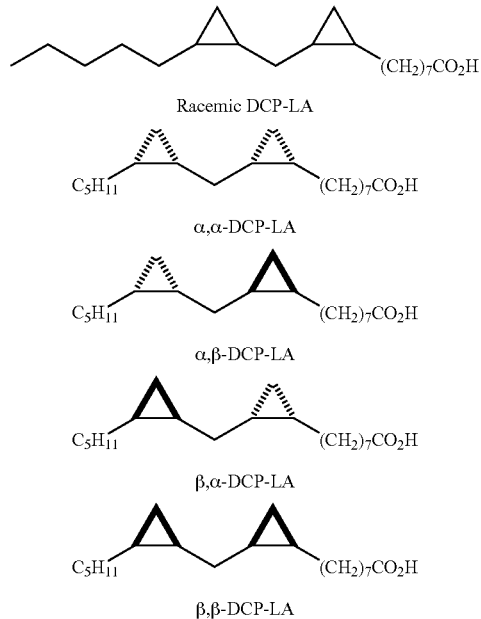

The optically active form used in the present invention is α,β-DCP-LA. α,β-DCP-LA can be produced by, for example, the following method (yield shown is one example).

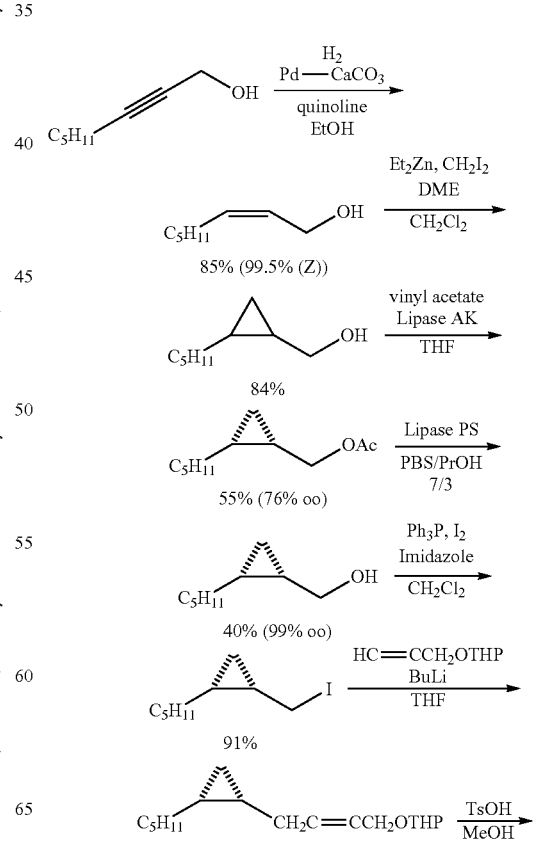

-continued

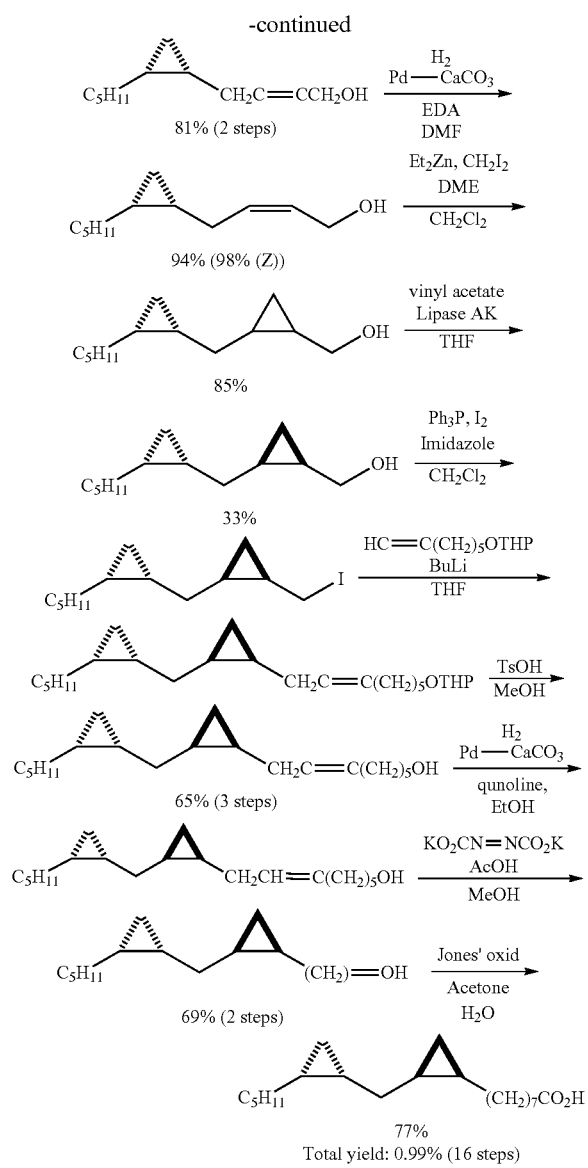

The starting materials and the reagents to be used are commercially available or can be appropriately synthesized according to a known report.

α,β-DCP-LA can also be used as a salt. While the salt of α,β-DCP-LA is not particularly limited, a salt acceptable as a medicament or food is preferable. Examples thereof include salts with inorganic bases (e.g., alkali metals such as sodium, potassium and the like; alkaline earth metals such as calcium, magnesium and the like; aluminum, ammonium), organic bases (e.g., trimethylamine, triethylamine, pyridine, picoline, ethanolamine, diethanolamine, triethanolamine, dicyclohexylamine, N,N-dibenzylethylenediamine), inorganic acids (e.g., hydrochloric acid, hydrobromic acid, nitric acid, sulfuric acid, phosphoric acid), organic acids (e.g., formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid), basic amino acids (e.g., arginine, lysine, ornithine) or acidic amino acids (e.g., aspartic acid, glutamic acid), and the like. Moreover, solvates [e.g., inclusion compounds (e.g., hydrate etc.)] of α,β-DCP-LA are also encompassed in the scope of the present invention.

The "selective PKC-ε activator" used in the present specification means, from a number of existing PKC isozymes, a PKC isozyme having an action to selectively activate PKC-ε. As isozymes of PKC, α, βI, βII, γ, δ, ε, η, μ, ζ and the like are known. Of these, α,β-DCP-LA can activate particularly PKC-ε selectively. PKC-ε localizes presynaptic terminal-selectively in the brain, and is involved in the release of neurotransmitters (Saito N et al., Brain Res. 607: 241-248, 1993, Tanaka C and Nishizuka Y, Annu. Rev. Neurosci 17: 551-567, 1994). Therefore, if it can selectively activate PKC-ε, the release of neurotransmitters can be promoted. On the other hand, PKC-γ is a PKC isozyme localized in postsynaptic cells in the brain, activation of PKC-γ is not involved in neurotransmitter release.

Examples of the "neurotransmitter release disorder" in the present specification include a decrease in the synthesis of neurotransmitters (e.g., acetylcholine, glutamic acid, GABA, noradrenaline, dopamine, serotonin and the like) and a decrease in the release of neurotransmitters from the presynaptic terminal, which are accompanied by denaturation and disappearance of neuron. Examples of the disease state of these disorders include age-related cognitive decline, neurodegenerative diseases (Alzheimer's disease, Parkinson's disease, diffuse Lewy body disease (dementia having Lewy body), frontotemporal dementia, Pick's disease, Creutzfeldt-Jakob disease, Huntington's disease, progressive supranuclear palsy etc.), vascular dementia (multiple lacunar infarcts, Binswanger's disease and diffuse infarction in the white matter etc.), viral encephalitis (herpes encephalitis, HIV encephalitis (dementia due to AIDS) and syphilitic encephalitis etc.), alcohol-induced persisting dementia (Korsakoff's syndrome and Wernicke encephalopathy etc.), and cognitive decline caused by other diseases (cognitive decline due to normal pressure hydrocephalus, chronic subdural hematoma, moya-moya disease, dementia pugilistica, hypothyroidism, hypercalcemia, hypoglycemia, vitamin B1 deficiency, vitamin B12 deficiency and folic acid deficiency and the like), Parkinson's disease, extrapyramidal disease, depression, panic syndrome, insomnia, emotional disturbance syndrome, frustrated disease, pain, gastrointestinal motility disorder and the like.

α,β-DCP-LA can prevent and/or treat such disease state in mammals (e.g., mouse, rat, hamster, rabbit, cat, dog, bovine, sheep, monkey, human and the like) by stimulating the release of neurotransmitters.

α,β-DCP-LA is useful for the prophylaxis and/or treatment of diseases (neuropsychiatric diseases) related to neurotransmission disorders, since it has a neurotransmitter release stimulation action via its selective PKC-ε activation action.

Examples of the neuropsychiatric disease include age-related cognitive decline, neurodegenerative diseases (Alzheimer's disease, Parkinson's disease, diffuse Lewy body disease (dementia having Lewy body), frontotemporal dementia, Pick's disease, Creutzfeldt-Jakob disease, Huntington's disease, progressive supranuclear palsy etc.), vascular dementia (multiple lacunar infarcts, Binswanger's disease and diffuse infarction in the white matter etc.), viral encephalitis (herpes encephalitis, HIV encephalitis (dementia due to AIDS) and syphilitic encephalitis etc.), alcohol-induced persisting dementia (Korsakoff's syndrome and Wernicke encephalopathy etc.), and cognitive decline caused by other diseases (cognitive decline due to normal pressure hydrocephalus, chronic subdural hematoma, moya-moya disease, dementia pugilistica, hypothyroidism, hypercalcemia, hypoglycemia, vitamin B1 deficiency, vitamin B12 deficiency and folic acid deficiency and the like), Parkinson's disease, extrapyramidal disease, depression, panic syndrome, emotional disturbance syndrome, frustrated disease and the like.

In general, "dementia" means diseases accompanied by various kinds of symptoms centering around learning and memory disorders and impaired judgment. Many causative diseases of dementia have been reported to date and, for example, neurodegenerative diseases such as Alzheimer's disease, Lewy body dementia, Pick's disease and the like, and cerebrovascular lesions such as multiple brain infarcts, diffuse white-matter infarction and the like. Furthermore, in the brain surgery areas, chronic subdural hematoma, normal pressure hydrocephalus and the like cause dementia. In addition, herpes encephalitis, Wernicke encephalopathy caused by alcohol, vitamin B1 deficiency, vitamin B12 deficiency, hypothyroidism and the like also cause dementia. Even in the absence of such basic diseases, the brain shrinks due to aging (brain atrophy), and particularly, atrophy of hippocampus that plays a major part of cognitive function causes a decrease in the cognitive function. The agent of the present invention is useful for the prophylaxis or treatment of such dementia.

The agent of the present invention can contain any additive, for example, pharmaceutically acceptable carrier, together with the active ingredient, α,β-DCP-LA. Examples of the pharmaceutically acceptable carrier include, but are not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatin, gum arabic, polyethylene glycol, sucrose, starch and the like, disintegrants such as starch, carboxymethylcellulose, hydroxypropylstarch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyllysin•ammonium salt, glycine, orange powder and the like, preservatives such as sodium benzoate, sodium bisulfite, methylparaben, propylparaben and the like, stabilizers such as citric acid, sodium citrate, acetic acid and the like, suspensions such as methylcellulose, polyvinylpyrrolidone, aluminum stearate and the like, dispersing agents such as surfactant and the like, diluents such as water, saline, orange juice and the like, base waxes such as cacao butter, polyethylene glycol, paraffin and the like, and the like.

In one embodiment, the agent of the present invention can be formulated as a pharmaceutical preparation preferable for oral administration. The pharmaceutical preparation preferable for oral administration includes a liquid wherein an effective amount of a substance is dissolved in a diluent such as water and saline, a capsule, granule, powder or tablet, containing an effective amount of a substance as a solid or granule, a suspension wherein an effective amount of a substance is suspended in a suitable dispersing medium, an emulsion wherein a solution containing an effective amount of a substance dissolved therein is dispersed and emulsified in a suitable dispersing medium, and the like.

In another embodiment, the agent of the present invention can be formulated as a pharmaceutical preparation preferable for parenteral administration. The pharmaceutical preparation preferable for parenteral administration (e.g., intravenous injection, subcutaneous injection, intramuscular injection, topical injection and the like) includes aqueous and non-aqueous isotonic sterile injection liquids, which may contain antioxidant, buffer, bacteriostatic agent, isotonicity agent and the like. Aqueous and non-aqueous sterile suspensions can also be mentioned, which may contain suspending agent, solubilizer, thickener, stabilizer, preservative and the like. Such preparation can be sealed in a container such as ampoule and vial by a unit dose or plural doses. In addition, it is also possible to freeze-dry the active ingredient and pharmaceutically acceptable carriers, and preserve them in a suitable sterile vehicle in a state only requiring dissolving or suspending immediately before use.

In the present invention, the dosage of therapeutically effective amount of α,β-DCP-LA varies depending on the age and condition of individual patients to be treated. In the case of intravenous administration, the daily dose of the compound is 0.001-10 mg per 1 kg body weight of human or animal; in the case of intramuscular administration, the daily dose of the compound is 0.001-10 mg per 1 kg body weight of human or animal; and in the case of oral administration, the daily dose of the compound is 0.01-100 mg per 1 kg body weight of human or animal, which are generally given for the prophylaxis and/or treatment of the above-mentioned diseases.

In the present invention, α,β-DCP-LA has superior PKC-ε activation action, neurotransmitter release promoting action and the like, and therefore, can be preferably used for the prophylaxis and/or treatment of neuropsychiatric diseases, as well as for the prophylaxis and/or treatment of insomnia, pain or gastrointestinal motility disorders, and the present invention can provide a method for the prophylaxis and/or treatment of these diseases and pathologies.

The contents disclosed in any publication cited in the present specification, including patents and patent applications, are hereby incorporated in their entireties by reference, to the extent that they have been disclosed herein.

While the present invention is explained in more detail in the following by referring to Examples and Experimental Examples, the present invention is not limited by the following Examples and the like in any manner.

EXAMPLES

Example 1

Synthesis of Optical Isomer of DCP-LA

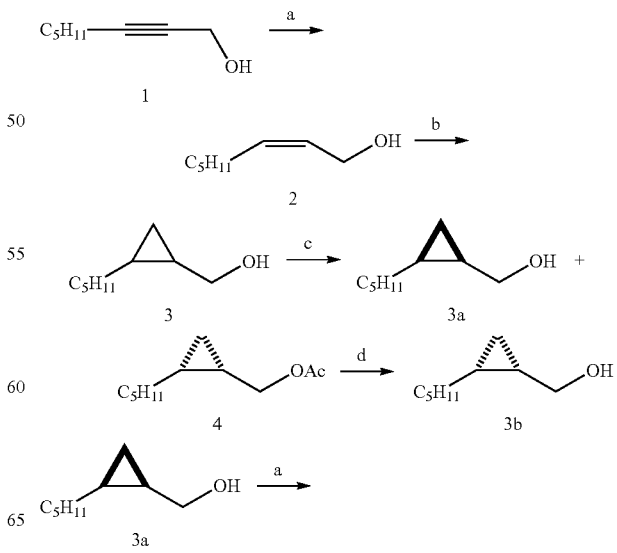

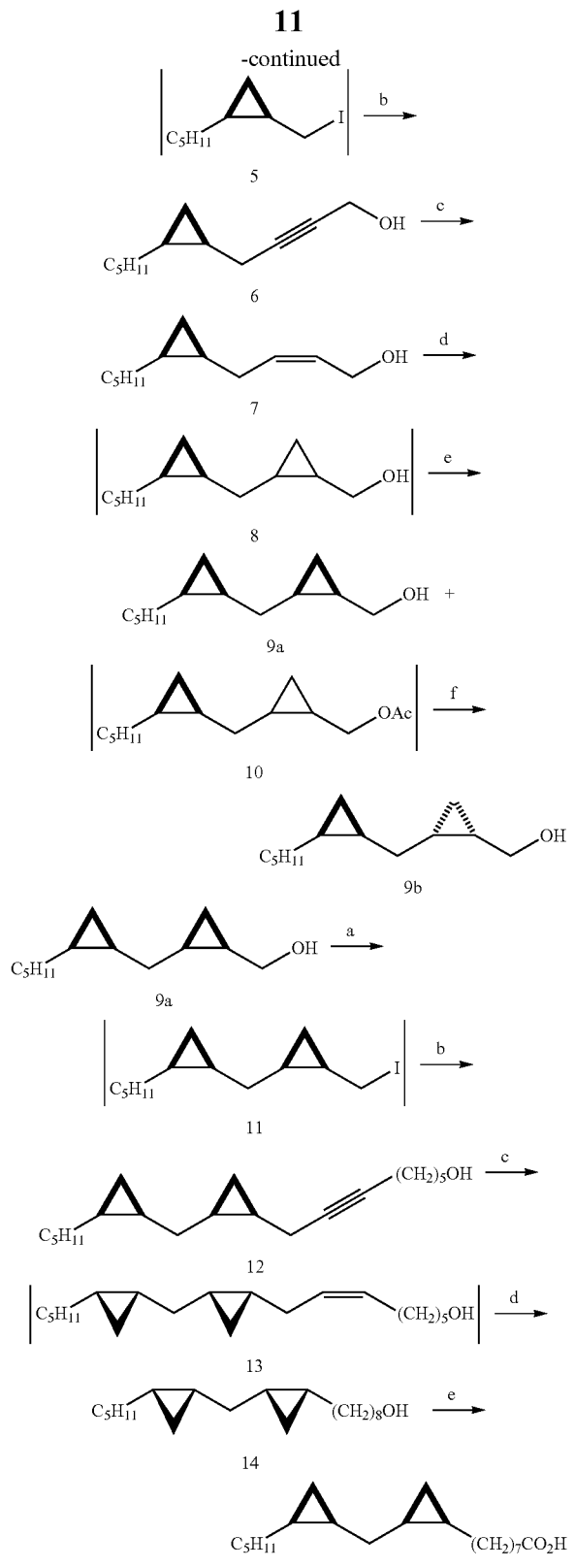

mL) was added 5% Lindlar catalyst (1 g), and the mixture was stirred at 4° C. for 10 hr in the presence of hydrogen (1 atm). The catalyst was filtered off through a celite pad and rinsed with ethyl acetate. The filtrate was washed with 1N HCl, water and brine, and the organic layers were combined, dried over anhydrous $MgSO_4$ and concentrated under reduced pressure. The crude product was purified by silica gel column chromatography (hexane/ethyl acetate=4/1) to give compound 2 (8.63 g, 85%) as a colorless oil.

$^1$H-NMR (400 MHz, $CDCl_3$) δ 0.90 (t, J=6.8 Hz, 3H), 1.21 (br s, 1H), 1.23-1.42 (m, 6H), 2.07 (dt, J=6.8 and 6.8 Hz, 2H), 4.20 (d, J=5.9 Hz, 2H), 5.54 (dt, J=10.9 and 6.8 Hz, 1H), 5.61 (dt, J=10.9 and 5.9 Hz, 1H).

[(1R*,2S*)-2-pentylcyclopropyl]methanol (Compound 3)

To a solution of compound 2 (4.00 g, 31.2 mmol) and DME (16.6 mL, 158 mmol) in $CH_2Cl_2$ (300 mL) was added a solution (1.06 M) of $Et_2Zn$ (150 mL, 158 mmol) and $CH_2I_2$ (28 mL, 16.6 mmol) in hexane at 2° C. After stirring at room temperature for 5 hr, a saturated aqueous solution of $NH_4Cl$ was added to the reaction mixture. The aqueous layer was extracted with ether, and the organic layers were combined, dried over anhydrous $MgSO_4$ and concentrated under reduced pressure. The crude product was purified by silica gel column chromatography (hexane/ethyl acetate=4/1) to give compound 3 (3.57 g, 80%) as a colorless oil.

[(1R,2S)-2-pentylcyclopropyl]methanol(3a) and [(1S,2R)-2-pentylcyclopropyl]methanol (3b)

To a solution of compound 3 (6.04 g, 42.4 mmol) and vinyl acetate (3.92 mL, 42.4 mmol) in THF (120 mL) was added *Pseudomonas fluorescens*-derived lipase (Lipase Amano AK) (0.60 g, 10 wt %) at room temperature. After stirring at room temperature for 5 hr, the reaction mixture was filtered through a celite pad and rinsed with ethyl acetate. The filtrate was concentrated under reduced pressure. The crude product was purified by silica gel column chromatography (hexane/ethyl acetate=4/1) to give compound 3a (2.59 g, 38%, >99.9% ee) together with compound 4 (4.34 g, 55%, 76% ee) as colorless Oils.

$^1$H-NMR (400 MHz, $CDCl_3$) δ −0.03 (ddd, J=5.4, 5.0, and 5.0 Hz, 1H), 0.71 (ddd, J=8.1, 8.1, and 5.0 Hz, 1H), 0.83-0.92 (m, 1H), 0.90 (t, J=6.8 Hz, 3H), 1.04-1.16 (m, 1H), 1.18-1.52 (m, 8H), 3.58 (dd, J=10.9 and 8.1 Hz, 1H), 3.67 (dd, J=10.9 and 6.8 Hz, 1H).

To a solution of compound 4 (3.00 g, 16.3 mmol) in PBS buffer (pH 7.0, 42 ml) and n-propanol (18 mL) was added *Burkholderia cepacia*-derived lipase (Lipase Amano PS) (300 mg, 10 wt %) at room temperature. After stirring at room temperature for 5 hr, a saturated aqueous solution of 1N HCl was added to the reaction mixture. The aqueous layer was extracted with ether, and the organic layers were combined, dried over anhydrous $MgSO_4$ and concentrated under reduced pressure. The crude product was purified by silica gel column chromatography (hexane/ethyl acetate=4/1) to give compound 3b (1.20 g, 51%, 99.0% ee) as a colorless oil.

$^1$H-NMR (400 MHz, $CDCl_3$) δ −0.03 (ddd, J=5.4, 5.0, and 5.0 Hz, 1H), 0.71 (ddd, J=8.1, 8.1, and 5.0 Hz, 1H), 0.83-0.92 (m, 1H), 0.90 (t, J=6.8 Hz, 3H), 1.04-1.16 (m, 1H), 1.18-1.52 (m, 8H), 3.58 (dd, J=11.1 and 8.1 Hz, 1H), 3.67 (dd, J=11.1 and 6.8 Hz, 1H).

4-[(1R,2S)-2-pentylcyclopropyl]-2-butyn-1-ol (Compound 6)

To a solution of compound 3a (1.55 g, 10.9 mmol), $PPh_3$ (5.71 g, 21.8 mmol) and imidazole (1.42 g, 21.8 mmol) in (Z) Oct-2-en-1-ol (Compound 2)

To a solution of 2-octyn-1-ol (compound 1; 10 g, 80.5 mmol) and quinoline (11.6 mL, 96.6 mmol) in ethanol (100

CH$_2$Cl$_2$ (22 mL) was added iodine (2.63 g, 21.8 mmol) at room temperature. After stirring at room temperature for 20 min, water was added to the reaction mixture. The aqueous layer was extracted with hexane, and the organic layers were combined, dried over anhydrous MgSO$_4$ and concentrated under reduced pressure. The crude product was purified by silica gel column chromatography (hexane/ethyl acetate=9/1) to give compound 5 (2.20 g) as a colorless oil.

To a solution of tetrahydro-2-(2-propynyloxy)-2H-pyran (2.57 mL, 18.3 mmol) in THF (30 mL) was slowly added a 1.60 M solution of n-BuLi (11 mL, 17.4 mmol) in hexane at −60° C. under a nitrogen atmosphere. The reaction mixture was stirred at −60° C. for 10 min, and compound 5 (2.20 g, 8.72 mmol) in THF (2 mL) was added. The reaction mixture was stirred at room temperature for 18 hr, and then a saturated aqueous solution of NH$_4$Cl was added. The aqueous layer was extracted with ether, and the organic layers were combined, dried over anhydrous MgSO$_4$ and concentrated under reduced pressure. The crude product was dissolved in methanol (18 mL), and TsOH.H$_2$O (0.16 g, 0.87 mmol) was added at room temperature. After stirring at 50° C. for 0.5 hr, the reaction mixture was added to a saturated aqueous solution of NaHCO$_3$. The aqueous layer was extracted with ether, and the organic layers were combined, dried over anhydrous MgSO$_4$ and concentrated under reduced pressure. The crude product was purified by silica gel column chromatography (hexane/ethyl acetate=10/1) to give compound 6 (1.24 g, 63% in 3 steps) as a colorless oil.

$^1$H-NMR (400 MHz, CDCl$_3$) δ −0.15 (ddd, J=5.4, 5.0, and 5.0 Hz, 1H), 0.68 (ddd, J=8.6, 8.6, and 5.0 Hz, 1H), 0.72-0.84 (m, 1H), 0.89 (t, J=6.8 Hz, 3H), 0.90-1.03 (m, 1H), 1.13-1.58 (m, 8H), 2.18 (dddd, J=17.2, 7.2, 1.8 and 1.8 Hz, 1H), 2.27 (dddd, J=17.2, 6.8, 1.8 and 1.8 Hz, 1H), 4.27 (br s, 1H, 1-H);

ESI-TOF/MS (positive ion) calcd. for C$_{12}$H$_{20}$ONa ([M+Na]$^+$) 203.1406. found 203.1418.

4-[(1S,2R)-2-pentylcyclopropyl]-2-butyn-1-ol

By a method similar to the above-mentioned conversion of compound 3a to compound 6, compound 3b (1.50 g) was converted to the title compound (1.40 g, 73% in 3 steps).

$^1$H-NMR (400 MHz, CDCl$_3$) δ −0.15 (ddd, J=5.4, 5.0, and 5.0 Hz, 1H), 0.68 (ddd, J=8.6, 8.6, and 5.0 Hz, 1H), 0.72-0.84 (m, 1H), 0.89 (t, J=6.8 Hz, 3H), 0.90-1.03 (m, 1H), 1.13-1.58 (m, 8H), 2.18 (dddd, J=17.2, 7.2, 1.8 and 1.8 Hz, 1H), 2.27 (dddd, J=17.2, 6.8, 1.8 and 1.8 Hz, 1H), 4.27 (br s, 1H, 1-H).

(Z)-4-[(1R,2S)-2-pentylcyclopropyl]-2-buten-1-ol (Compound 7)

To a solution of compound 6 (1.12 g, 6.21 mmol) and ethylenediamine (0.50 mL, 7.45 mmol) in DMF (12 mL) was added 5% Lindlar catalyst (56 mg, 10 wt %), and the mixture was stirred at room temperature for 8 hr in the presence of hydrogen (1 atm). The catalyst was filtered off through a celite pad and rinsed with ethyl acetate. The filtrate was washed with 1N HCl, water and brine, and the organic layers were combined, dried over anhydrous MgSO$_4$ and concentrated under reduced pressure. The crude product was purified by silica gel column chromatography (hexane/ethyl acetate=9/1) to give compound 7 (1.02 g, 90%) as a colorless oil.

$^1$H-NMR (400 MHz, CDCl$_3$) δ −0.23 (ddd, J=5.4, 5.0, and 5.0 Hz, 1H), 0.62 (ddd, J=8.6, 8.6, and 5.0 Hz, 1H), 0.67-0.80 (m, 1H), 0.89 (t, J=6.8 Hz, 3H), 1.12-1.23 (m, 1H), 1.24-1.45 (m, 8H), 1.99 (ddd, J=15.1, 7.3 and 7.0 Hz, 1H), 2.14 (ddd, J=15.1, 7.3 and 7.0 Hz, 1H), 4.20 (dd, J=6.0 and 6.0 Hz, 2H), 5.61 (dt, J=11.0 and 6.0 Hz, 1H), 5.67 (dt, J=11.0 and 7.3 Hz, 1H);

ESI-HRMS (positive ion, sodium formate) calcd. for C$_{12}$H$_{22}$ONa ([M+Na]$^+$) 205.1563; found 205.1556.

(Z)-4-[(1S,2R)-2-pentylcyclopropyl]-2-buten-1-ol

By a method similar to the above-mentioned conversion of compound 6 to compound 7, 4-[(1S,2R)-2-pentylcyclopropyl]-2-butyn-1-ol (1.26 g) was converted to the title compound (1.20 g, 94%)

$^1$H-NMR (400 MHz, CDCl$_3$) δ −0.23 (ddd, J=5.4, 5.0, and 5.0 Hz, 1H), 0.62 (ddd, J=8.6, 8.6, and 5.0 Hz, 1H), 0.67-0.80 (m, 1H), 0.89 (t, J=6.8 Hz, 3H), 1.12-1.23 (m, 1H), 1.24-1.45 (m, 8H), 1.99 (ddd, J=15.1, 7.3 and 7.0 Hz, 1H), 2.14 (ddd, J=15.1, 7.3 and 7.0 Hz, 1H), 4.20 (dd, J=6.0 and 6.0 Hz, 2H), 5.61 (dt, J=11.0 and 6.0 Hz, 1H), 5.67 (dt, J=11.0 and 7.3 Hz, 1H).

[(1R,2S)-2-{(1S,2S)-2-pentylcyclopropylmethyl}-cyclopropyl]methanol (Compound 9a) and [(1S,2R)-2-{(1S,2S)-2-pentylcyclopropylmethyl}-cyclopropyl]methanol (Compound 9b)

To a solution of compound 7 (1.03 g, 5.65 mmol) and DME (3.0 mL, 28.3 mmol) in CH$_2$Cl$_2$ (54 mL) was added a solution (1.06 M) of Et$_2$Zn (4.6 mL, 28.3 mmol) and CH$_2$I$_2$ (4.0 mL, 56.5 mmol) in hexane at 0° C. After stirring at room temperature for 5 hr, a saturated aqueous solution of NH$_4$Cl was added to the reaction mixture. The aqueous layer was extracted with ether, and the organic layers were combined, dried over anhydrous MgSO$_4$ and concentrated under reduced pressure. The crude product was purified by silica gel column chromatography (hexane/ethyl acetate=4/1) to give compound 8 (877 mg) as a colorless oil.

To a solution of compound 8 (877 mg, 4.47 mmol) and vinyl acetate (0.31 mL, 3.35 mmol) in THF (8.8 mL) was added *Pseudomonas fluorescens*-derived lipase (Lipase Amano AK) (88 mg, 10 wt %) at room temperature. After stirring at room temperature for 6 hr, the reaction mixture was filtered through a celite pad and rinsed with ethyl acetate. The filtrate was concentrated under reduced pressure. The crude product was purified by silica gel column chromatography (hexane/ethyl acetate=9/1) to give compound 9a (385 mg, 35% in 2 steps, >99.9% de) together with compound 10 (468 mg) as colorless oils.

$^1$H-NMR (400 MHz, CDCl$_3$) δ −0.24 (ddd, J=5.0, 5.0, and 4.6 Hz, 1H), 0.03 (ddd, J=5.0, 5.0, and 4.5 Hz, 1H), 0.61 (ddd, J=7.8, 7.8, and 4.6 Hz, 1H), 0.67-0.85 (m, 3H), 0.89 (t, J=6.8 Hz, 3H), 0.94-1.06 (m, 1H), 1.07-1.22 (m, 3H), 1.23-1.46 (m, 7H), 1.57 (ddd, J=14.2, 6.0 and 6.0 Hz, 1H), 3.57 (dd, J=11.4 and 8.2 Hz, 1H), 3.67 (dd, J=11.4 and 6.9 Hz, 1H);

$^{13}$C-NMR (100 MHz, CDCl$_3$) δ 9.31, 10.86, 14.24, 15.69, 15.79, 16.35, 18.02, 22.71, 27.66, 28.72, 29.85, 31.86, 63.33;

ESI-HRMS (positive ion, sodium formate) calcd. for C$_{13}$H$_{24}$ONa ([M+Na]$^+$) 219.1719; found 219.1718.

To a solution of compound 10 (270 mg) in PBS buffer (pH 7.0, 4.0 mL) and n-propanol (1.4 mL) was added *Burkholderia cepacia*-derived lipase (Lipase Amano PS) (27 mg, 10 wt %) at room temperature. After stirring at room temperature for 12 hr, a saturated aqueous solution of 1N HCl was added to the reaction mixture. The aqueous layer was extracted with ether, and the organic layers were combined, dried over anhydrous MgSO$_4$ and concentrated under reduced pressure. The crude product was purified by silica gel column chromatography (hexane/ethyl acetate=4/1) to give compound 9b (175 mg, 25% in 3 steps, >98.0 de) as a colorless oil.

$^1$H-NMR (400 MHz, CDCl$_3$) δ −0.24 (ddd, J=5.0, 5.0, and 4.6 Hz, 1H), 0.03 (ddd, J=5.0, 5.0, and 4.5 Hz, 1H), 0.61 (ddd, J=7.8, 7.8, and 4.6 Hz, 1H), 0.67-0.85 (m, 3H), 0.89 (t, J=6.8 Hz, 3H), 0.94-1.06 (m, 1H), 1.07-1.22 (m, 3H), 1.23-1.46 (m, 7H), 1.57 (ddd, J=14.2, 6.0 and 6.0 Hz, 1H), 3.57 (dd, J=11.4 and 8.2 Hz, 1H), 3.67 (dd, J=11.4 and 6.9 Hz, 1H);

$^{13}$C-NMR (100 MHz, CDCl$_3$) δ 9.31, 10.86, 14.24, 15.69, 15.79, 16.35, 18.02, 22.71, 27.66, 28.72, 29.85, 31.86, 63.33;

ESI-HRMS (positive ion, sodium formate) calcd. for C$_{13}$H$_{24}$ONa ([M+Na]$^+$) 219.1719; found 219.1718.

[(1R,2S)-2-{(1R,2R)-2-pentylcyclopropylmethyl}-cyclopropyl]methanol

By a method similar to the above-mentioned conversion of compound 7 to compound 9a, (Z)-4-[(1S,2R)-2-pentylcyclopropyl]-2-buten-1-ol (1.05 g) was converted to the title compound (349 mg, 28% in 2 steps).

$^1$H-NMR (400 MHz, CDCl$_3$) δ −0.27 (ddd, J=5.0, 5.0, and 4.6 Hz, 1H), −0.01 (ddd, J=5.0, 5.0, and 4.5 Hz, 1H), 0.64 (ddd, J=7.4, 7.4, and 4.6 Hz, 1H), 0.67-0.85 (m, 3H), 0.89 (t, J=6.8 Hz, 3H), 0.93-1.05 (m, 1H), 1.07-1.21 (m, 2H), 1.26 (ddd, J=14.2, 7.3 and 7.3 Hz, 1H), 1.26-1.43 (m, 6H), 1.45 (ddd, J=14.2, 7.3 and 7.3 Hz, 1H), 3.56 (dd, J=11.4 and 8.3 Hz, 1H), 3.68 (dd, J=11.4 and 6.8 Hz, 1H); $^{13}$C-NMR (100 MHz, CDCl$_3$) δ 9.30, 11.13, 14.11, 15.87, 15.93, 16.41, 18.31, 22.70, 27.90, 28.85, 29.83, 31.85, 63.39;

ESI-HRMS (positive ion, sodium formate) calcd. for C$_{13}$H$_{24}$ONa ([M+Na]$^+$) 219.1719; found 219.1721.

[(1S,2R)-2-{(1R,2R)-2-pentylcyclopropylmethyl}-cyclopropyl]methanol

By a method similar to the above-mentioned conversion of compound 7 to compound 9b, (Z)-4-[(1S,2R)-2-pentylcyclopropyl]-2-buten-1-ol (1.05 g) was converted to the title compound (304 mg, 25% in 3 steps).

$^1$H-NMR (400 MHz, CDCl$_3$) δ −0.24 (ddd, J=5.0, 5.0, and 4.6 Hz, 1H), 0.03 (ddd, J=5.0, 5.0, and 4.5 Hz, 1H), 0.61 (ddd, J=7.8, 7.8, and 4.6 Hz, 1H), 0.67-0.85 (m, 3H), 0.89 (t, J=6.8 Hz, 3H), 0.94-1.06 (m, 1H), 1.07-1.22 (m, 3H), 1.23-1.46 (m, 7H), 1.57 (ddd, J=14.2, 6.0 and 6.0 Hz, 1H), 3.57 (dd, J=11.4 and 8.2 Hz, 1H), 3.67 (dd, J=11.4 and 6.9 Hz, 1H);

$^{13}$C-NMR (100 MHz, CDCl$_3$) δ 9.31, 10.86, 14.24, 15.69, 15.79, 16.35, 18.02, 22.71, 27.66, 28.72, 29.85, 31.86, 63.33;

ESI-HRMS (positive ion, sodium formate) calcd. for C$_{13}$H$_{24}$ONa ([M+Na]$^+$) 219.1719; found 219.1721.

8-[(1R,2S)-2-{(1S,2S)-2-pentylcyclopropylmethyl}-cyclopropyl]-6-octyn-1-ol (Compound 12)

To a solution of compound 9a (95 mg, 0.483 mmol), PPh$_3$ (253 mg, 0.966 mmol) and imidazole (66 mg, 0.966 mmol) in CH$_2$Cl$_2$ (2.5 mL) was added iodine (122 mg, 0.966 mmol) at room temperature. After stirring at room temperature for 20 min, water was added to the reaction mixture. The aqueous layer was extracted with hexane, and the organic layers were combined, dried over anhydrous MgSO$_4$ and concentrated under reduced pressure. The crude product was purified by silica gel column chromatography (hexane/ethyl acetate=9/1) to give compound 11 (135 mg) as a colorless oil.

To a solution of tetrahydro-2-(5-heptynyloxy)-2H-pyran (345 mg, 1.76 mmol) in THF (2.2 ml) was slowly added a 1.59 M solution of n-BuLi (1.1 mL, 1.76 mmol) in hexane at −70° C. under a nitrogen atmosphere. The reaction mixture was stirred at −70° C. for 2 hr, and HMPA (0.46 mL, 2.64 mmol) was added at −70° C. The reaction mixture was stirred at −70° C. for 15 min, and iodide (135 mg, 0.440 mmol) of compound 11 in THF (1 mL) was added. The reaction mixture was stirred at room temperature for 16 hr, and then a saturated aqueous solution of NH$_4$Cl was added. The aqueous layer was extracted with ether, and the organic layers were combined, dried over anhydrous MgSO$_4$ and concentrated under reduced pressure. The crude product was dissolved in methanol (2 mL), and TsOH.H$_2$O (8 mg, 0.044 mmol) was added at room temperature. After stirring at 50° C. for 0.5 hr, the reaction mixture was added to a saturated aqueous solution of NaHCO$_3$. The aqueous layer was extracted with ether, and the organic layers were combined, dried over anhydrous MgSO$_4$ and concentrated under reduced pressure. The crude product was purified by silica gel column chromatography (hexane/ethyl acetate=15/1) to give compound 12 (1.24 g, 65% in 3 steps) as a colorless oil.

$^1$H-NMR (400 MHz, CDCl$_3$) δ −0.24 (ddd, J=5.0, 5.0, and 4.5 Hz, 1H), −0.10 (ddd, J=5.0, 5.0, and 4.5 Hz, 1H), 0.62 (ddd, J=8.2, 8.2, and 4.5 Hz, 1H), 0.65-0.73 (m, 2H), 0.80-0.89 (m, 2H), 0.89 (t, J=6.8 Hz, 3H), 0.94-1.06 (m, 1H), 1.06 (ddd, J=14.2, 7.3 and 7.3 Hz, 1H), 1.10-1.21 (m, 1H), 1.23-1.65 (m, 14H), 2.10-2.20 (m, 4H), 3.65 (t, J=6.3 Hz, 2H);

ESI-HRMS (positive ion, sodium formate) calcd. for C$_{20}$H$_{34}$ONa ([M+Na]$^+$) 313.2501; found 313.2498.

8-[(1S,2R)-2-{(1S,2S)-2-pentylcyclopropylmethyl}-cyclopropyl]-6-octyn-1-ol

By a method similar to the above-mentioned conversion of compound 9a to compound 12, compound 9b (114 mg) was converted to the title compound (106 mg, 72% in 3 steps).

$^1$H-NMR (400 MHz, CDCl$_3$) δ −0.27 (ddd, J=5.0, 5.0, and 4.5 Hz, 1H), −0.12 (ddd, J=5.0, 5.0, and 4.5 Hz, 1H), 0.62 (ddd, J=8.2, 8.2, and 4.1 Hz, 1H), 0.65-0.77 (m, 2H), 0.77-0.89 (m, 2H), 0.89 (t, J=6.8 Hz, 3H), 0.93-1.04 (m, 1H), 1.06-1.18 (m, 1H), 1.23-1.65 (m, 15H), 2.08-2.26 (m, 4H), 3.65 (t, J=6.3 Hz, 2H);

ESI-HRMS (positive ion, sodium formate) calcd. for C$_{20}$H$_{34}$ONa ([M+Na]$^+$) 313.2501; found 313.2493.

8-[(1R,2S)-2-{(1R,2R)-2-pentylcyclopropylmethyl}-cyclopropyl]-6-octyn-1-ol

By a method similar to the above-mentioned conversion of compound 9a to compound 12, [(1R,2S)-2-{(1R,2R)-2-pentylcyclopropylmethyl}-cyclopropyl]methanol (160 mg) was converted to the title compound (152 mg, 70% in 3 steps).

$^1$H-NMR (400 MHz, CDCl$_3$) δ −0.27 (ddd, J=5.0, 5.0, and 4.5 Hz, 1H), −0.12 (ddd, J=5.0, 5.0, and 4.5 Hz, 1H), 0.62 (ddd, J=8.2, 8.2, and 4.1 Hz, 1H), 0.65-0.77 (m, 2H), 0.77-0.89 (m, 2H), 0.89 (t, J=6.8 Hz, 3H), 0.93-1.04 (m, 1H), 1.06-1.18 (m, 1H), 1.23-1.65 (m, 15H), 2.08-2.26 (m, 4H), 3.65 (t, J=6.3 Hz, 2H);

ESI-HRMS (positive ion, sodium formate) calcd. for C$_{20}$H$_{34}$ONa ([M+Na]$^+$) 313.2501; found 313.2496.

8-[(1S,2R)-2-{(1R,2R)-2-pentylcyclopropylmethyl}-cyclopropyl]-6-octyn-1-ol

By a method similar to the above-mentioned conversion of compound 9a to compound 12, [(1S,2R)-2-{(1R,2R)-2-pentylcyclopropylmethyl}-cyclopropyl]methanol (120 mg) was converted to the title compound (125 mg, 61% in 3 steps).

$^1$H-NMR (400 MHz, CDCl$_3$) δ −0.24 (ddd, J=5.0, 5.0, and 4.5 Hz, 1H), −0.10 (ddd, J=5.0, 5.0, and 4.5 Hz, 1H), 0.62

(ddd, J=8.2, 8.2, and 4.5 Hz, 1H), 0.65-0.73 (m, 2H), 0.80-0.89 (m, 2H), 0.89 (t, J=6.8 Hz, 3H), 0.94-1.06 (m, 1H), 1.06 (ddd, J=14.2, 7.3 and 7.3 Hz, 1H), 1.10-1.21 (m, 1H), 1.23-1.65 (m, 14H), 2.10-2.20 (m, 4H), 3.65 (t, J=6.3 Hz, 2H);

ESI-HRMS (positive ion, sodium formate) calcd. for $C_{20}H_{34}ONa$ ([M+Na]$^+$) 313.2501; found 313.2502.

8-[(1R,2S)-2-{(1S,2S)-2-pentylcyclopropylmethyl}-cyclopropyl]octan-1-ol (Compound 14)

To a solution of compound 12 (31 mg, 0.107 mmol) and quinoline (15 μL, 0.128 mmol) in methanol (1 mL) was added 5% Lindlar catalyst (3 mg), and the mixture was stirred at room temperature for 10 min in the presence of hydrogen (1 atm). The catalyst was filtered off through a celite pad and rinsed with ethyl acetate. The filtrate was washed with 1N HCl, water and brine, and the organic layers were combined, dried over anhydrous $MgSO_4$ and concentrated under reduced pressure. The crude product was dissolved in methanol (5 mL), and potassium azodicarboxylate (3.12 g, 16.0 mmol) and acetic acid (1.83 mL, 32.0 mmol) were added at room temperature. After stirring at room temperature for 8 hr, water was added to the reaction mixture. The aqueous layer was extracted with hexane, and the organic layers were combined, dried over anhydrous $MgSO_4$ and concentrated under reduced pressure. The crude product was purified by silica gel column chromatography (hexane/ethyl acetate=4/1) to give compound 14 (30 mg, 99%) as a colorless oil.

$^1$H-NMR (400 MHz, $CDCl_3$) δ −0.25 (ddd, J=5.0, 5.0, and 4.5 Hz, 2H), 0.60 (ddd, J=8.2, 8.2, and 4.5 Hz, 1H), 0.62-0.73 (m, 2H), 0.73-0.85 (m, 2H), 0.89 (t, J=6.8 Hz, 3H), 1.02 (ddd, J=12.3, 7.8 and 7.8 Hz, 1H), 1.10-1.24 (m, 2H), 1.23-1.45 (m, 18H), 1.49 (ddd, J=12.3, 7.8 and 7.8 Hz, 1H), 1.50-1.65 (m, 2H), 3.64 (t, J=6.8 Hz, 2H);

ESI-HRMS (positive ion, sodium formate) calcd. for $C_{20}H_{38}ONa$ ([M+Na]$^+$) 317.2815; found 317.2814.

8-[(1S,2R)-2-{(1S,2S)-2-pentyloclopropylmethyl}-cyclopropyl]octanol

By a method similar to the above-mentioned conversion of compound 12 to compound 14, 8-[(1S,2R)-2-{(1S,2S)-2-pentylcyclopropylmethyl}-cyclopropyl]-6-octyn-1-ol (32 mg) was converted to the title compound (27.5 mg, 83% in 2 steps).

$^1$H-NMR (400 MHz, $CDCl_3$) δ −0.28 (ddd, J=5.0, 5.0, and 4.1 Hz, 2H), 0.60 (ddd, J=8.2, 8.2, and 4.1 Hz, 1H), 0.63-0.75 (m, 2H), 0.75-0.85 (m, 2H), 0.89 (t, J=6.8 Hz, 3H), 1.07-1.18 (m, 2H), 1.20-1.45 (m, 20H), 1.51-1.63 (m, 2H), 3.64 (t, J=6.8 Hz, 2H);

ESI-HRMS (positive ion, sodium formate) calcd. for $C_{20}H_{38}ONa$ ([M+Na]$^+$) 317.2815; found 317.2824.

8-[(1R,2S)-2-{(1R,2R)-2-pentylcyclopropylmethyl}-cyclopropyl]octanol

By a method similar to the above-mentioned conversion of compound 12 to compound 14, 8-[(1R,2S)-2-{(1R,2R)-2-pentylcyclopropylmethyl}-cyclopropyl]-6-octyn-1-ol (40 mg) was converted to the title compound (34 mg, 69% in 2 steps).

$^1$H-NMR (400 MHz, $CDCl_3$) δ −0.28 (ddd, J=5.0, 5.0, and 4.1 Hz, 2H), 0.60 (ddd, J=8.2, 8.2, and 4.1 Hz, 1H), 0.63-0.75 (m, 2H), 0.75-0.85 (m, 2H), 0.89 (t, J=6.8 Hz, 3H), 1.07-1.18 (m, 2H), 1.20-1.45 (m, 20H), 1.51-1.63 (m, 2H), 3.64 (t, J=6.8 Hz, 2H);

ESI-HRMS (positive ion, sodium formate) calcd. for $C_{20}H_{38}ONa$ ([M+Na]$^+$) 317.2815; found 317.2828.

8-[(1S,2R)-2-{(1R,2R)-2-pentylcyclopropylmethyl}-cyclopropyl]octanol

By a method similar to the above-mentioned conversion of compound 12 to compound 14, 8-[(1S,2R)-2-{(1R,2R)-2-pentylcyclopropylmethyl}-cyclopropyl]-6-octyn-1-ol (30 mg) was converted to the title compound (29 mg, 94%).

$^1$H-NMR (400 MHz, $CDCl_3$) δ −0.25 (ddd, J=5.0, 5.0, and 4.5 Hz, 2H), 0.60 (ddd, J=8.2, 8.2, and 4.5 Hz, 1H), 0.62-0.73 (m, 2H), 0.73-0.85 (m, 2H), 0.89 (t, J=6.8 Hz, 3H), 1.02 (ddd, J=12.3, 7.8 and 7.8 Hz, 1H), 1.10-1.24 (m, 2H), 1.23-1.45 (m, 18H), 1.49 (ddd, J=12.3, 7.8 and 7.8 Hz, 1H), 1.50-1.65 (m, 2H), 3.64 (t, J=6.8 Hz, 2H);

ESI-HRMS (positive ion, sodium formate) calcd. for $C_{20}H_{38}ONa$ ([M+Na]$^+$) 317.2815; found 317.2807.

8-[(1R,2S)-2-{(1S,2S)-2-pentylcyclopropylmethyl}-cyclopropyl]octanoic acid (Compound 15) (β,β-DCP-LA)

To a solution of compound 14 (30 mg, 0.102 mmol) in acetone (2 mL) was added Jones reagent (0.1 mL, 0.254 mmol) at 4° C. After stirring at 4° C. for 0.5 hr, a 10% aqueous solution of $Na_2S_2O_3$ was added to the reaction mixture. The aqueous layer was extracted with ether, and the organic layers were combined, dried over anhydrous $MgSO_4$ and concentrated under reduced pressure. The crude product was purified by silica gel column chromatography (hexane/ethyl acetate=10/1) to give compound 15 (12 mg, 46%) as a colorless oil.

$[α]_D^{24}$=−0.15 (c=0.85, $CHCl_3$);

$^1$H-NMR (400 MHz, $CDCl_3$) δ −0.25 (ddd, J=5.0, 5.0, and 4.5 Hz, 2H), 0.60 (ddd, J=8.2, 8.2, and 4.5 Hz, 1H), 0.62-0.73 (m, 2H), 0.73-0.85 (m, 2H), 0.89 (t, J=6.8 Hz, 3H), 1.02 (ddd, J=12.3, 7.8 and 7.8 Hz, 1H), 1.10-1.24 (m, 2H), 1.23-1.65 (m, 16H), 1.49 (ddd, J=12.3, 7.8 and 7.8 Hz, 1H), 1.58-1.68 (m, 2H), 2.35 (t, J=7.3 Hz, 2H);

$^{13}$C-NMR (100 MHz, $CDCl_3$) δ 10.84, 14.14, 15.6, 15.65, 15.91, 22.73, 24.68, 27.86, 28.71, 29.07, 29.29, 29.42, 29.90, 30.13, 31.90, 34.01, 179.90;

ESI-HRMS (negative ion, sodium formate) calcd. for $C_{20}H_{35}O$ ([M-H]$^-$) 307.2642; found 307.2636.

8-[(1S,2R)-2-{(1S,2S)-2-pentylcyclopropylmethyl}-cyclopropyl]octanoic acid (β,α-DCP-LA)

By a method similar to the above-mentioned conversion of compound 14 to compound 15, 8-[(1S,2R)-2-{(1S,2S)-2-pentylcyclopropylmethyl}-cyclopropyl]octan-1-ol (20 mg) was converted to the title compound (4.2 mg, 20%).

$[α]_D^{19}$=+9.8 (c=0.42, $CHCl_3$);

$^1$H-NMR (400 MHz, $CDCl_3$) δ −0.29 (ddd, J=5.0, 5.0, and 4.1 Hz, 2H), 0.60 (ddd, J=8.2, 8.2, and 4.1 Hz, 1H), 0.61-0.73 (m, 2H), 0.73-0.84 (m, 2H), 0.89 (t, J=6.8 Hz, 3H), 1.05-1.19 (m, 2H), 1.20-1.45 (m, 18H), 1.57-1.71 (m, 2H), 2.35 (t, J=7.8 Hz, 2H);

$^{13}$C-NMR (100 MHz, $CDCl_3$) δ 11.01, 14.15, 15.86, 15.91, 16.03, 22.74, 24.67, 28.01, 28.87, 29.07, 29.30, 29.42, 29.90, 30.14, 31.90, 34.05, 180.15;

ESI-HRMS (negative ion, sodium formate) calcd. for $C_{20}H_{35}O$ ([M-H]$^-$) 307.2642; found 307.2631.

8-[(1R,2S)-2-{(1R,2R)-2-pentylcyclopropylmethyl}-cyclopropyl]octanoic acid (α,β-DCP-LA)

By a method similar to the above-mentioned conversion of compound 14 to compound 15, 8-[(1R,2S)-2-{(1R,2R)-2- pentylcyclopropylmethyl}-cyclopropyl]octanol (17.3 mg) was converted to the title compound (14.1 mg, 77%).

$[\alpha]_D^{19}$=−9.9 (c=1.0, CHCl$_3$);

$^1$H-NMR (400 MHz, CDCl$_3$) δ −0.29 (ddd, J=5.0, 5.0, and 4.1 Hz, 2H), 0.60 (ddd, J=8.2, 8.2, and 4.1 Hz, 1H), 0.61-0.73 (m, 2H), 0.73-0.84 (m, 2H), 0.89 (t, J=6.8 Hz, 3H), 1.05-1.19 (m, 2H), 1.20-1.45 (m, 18H), 1.57-1.71 (m, 2H), 2.35 (t, J=7.8 Hz, 2H);

$^{13}$C-NMR (100 MHz, CDCl$_3$) δ 11.02, 14.15, 15.86, 15.91, 16.03, 22.74, 24.67, 28.01, 28.87, 29.07, 29.30, 29.42, 29.90, 30.14, 31.90, 34.05, 180.14;

ESI-HRMS (negative ion, sodium formate) calcd. for C$_{20}$H$_{35}$O ([M-H]$^-$) 307.2642; found 307.2639.

8-[(1S,2R)-2-{(1R,2R)-2-pentylcyclopropylmethyl}-cyclopropyl]octanoic acid (α,α-DCP-LA)

By a method similar to the above-mentioned conversion of compound 14 to compound 15, 8-[(1S,2R)-2-{(1R,2R)-2-pentylcyclopropylmethyl}-cyclopropyl]octanol (20 mg) was converted to the title compound (20 mg, 94%).

$[\alpha]_D^{24}$=+0.25 (c=1.0, CHCl$_3$);

$^1$H-NMR (400 MHz, CDCl$_3$) δ −0.25 (ddd, J=5.0, 5.0, and 4.5 Hz, 2H), 0.60 (ddd, J=8.2, 8.2, and 4.5 Hz, 1H), 0.62-0.73 (m, 2H), 0.73-0.85 (m, 2H), 0.89 (t, J=6.8 Hz, 3H), 1.02 (ddd, J=12.3, 7.8 and 7.8 Hz, 1H), 1.10-1.24 (m, 2H), 1.23-1.64 (m, 16H), 1.49 (ddd, J=12.3, 7.8 and 7.8 Hz, 1H), 1.58-1.68 (m, 2H), 2.35 (t, J=7.3 Hz, 2H);

$^{13}$C-NMR (100 MHz, CDCl$_3$) δ 10.84, 14.14, 15.6, 15.65, 15.91, 22.73, 24.68, 27.86, 28.71, 29.07, 29.29, 29.42, 29.90, 30.13, 31.89, 34.01, 179.91;

ESI-HRMS (negative ion, sodium formate) calcd. for C$_{20}$H$_{35}$O ([M-H]$^-$) 307.2642; found 307.2637.

Experimental Example 1

Among 4 Optical Isomers, α,β-DCP-LA Selectively and Directly Activates PKC-ε Most Strongly (Material and Method)
1. Intracellular PKC Assay According to the method described in a publication [Kanno T et al., J Lipid Res 47 (6):1146-1156, 2006], the PKC activity of rat PC-12 cells was assayed. The cells were treated with each DCP-LA optical isomer at 37° C. for 10 min. The treatment was performed in an extracellular solution [137 mM NaCl, 5.4 mM KCl, 10 mM MgCl$_2$, 5 mM ethyleneglycol-bis(2-aminoethylether)-N,N,N',N'-tetraacetic acid (EGTA), 0.3 mM Na$_2$HPO$_4$, 0.4 mM K$_2$HPO$_4$ and 20 mM 4-(2-hydroxyethyl)-1-piperazin-ethanesulfonic acid, pH 7.2]. Then, the cells were rinsed with 100 μl of phosphate-buffered saline (PBS) in the absence of Ca$^{2+}$, and incubated in an extracellular solution (50 μl) containing 50 μg/ml digitonin, 25 mM glycerol 2-phosphate, 200 μM ATP and 100 μM synthetic PKC substrate peptide (Pyr-Lys-Arg-Pro-Ser-Gln-Arg-Ser-Lys-Tyr-Leu (SEQ ID NO: 1); MW, 1,374; Pyr: pyruvic acid) at 37° C. for 15 min. The supernatant was recovered and boiled at 100° C. for 5 min to discontinue the reaction. An aliquot (20 μl) of the solution was loaded on reversed-phase HPLC (LC-10ATvp, Shimadzu Co., Kyoto, Japan). A substrate peptide peak and a new resultant product peak were detected at the absorbance of 214 nm (SPD-10Avp UV-VIS detector, Shimadzu Co., Kyoto, Japan). It was confirmed that each peak corresponds to the non-phosphorylated or phosphorylated substrate peptide by analysis with matrix-assisted laser adsorption ionization time-of-flight mass spectrometer (MALDI-TOF MS) (Voyager ST-DER, PE Biosystems Inc., Foster City, USA). The molecular weight was calculated from the two standard spectra of bradykinin (MW 1060.2) and substance P (MW 1672.9).

The areas of the non-phosphorylated and phosphorylated substrate peptides were measured (total area corresponds to the concentration of PKC substrate peptide used). The phosphorylated substrate peptide level (pmol/l min/cell protein weight) was used as an index of PKC activity.

2. Knockdown of PKC-ε

The base sequence of the low molecule interference RNA (small, interfering RNA (siRNA)) silencing the PKC-ε target gene and used in this Experimental Example is as described below: 5'-CACAUCAGUGACGAACUCAUTT-3' (SEQ ID NO: 2) and 5'-AUGAGUUCGUCACUGAUGUGTT-3' (SEQ ID NO: 3). siRNA containing a scrambled sequence with the same GC content and the same nucleic acid constitution as those of PKC-ε siRNA was used as a negative control siRNA (NC siRNA). PC-12 cells were transfected with PKC-ε siRNA or NC siRNA. At 24 hr after transfection, in situ PKC assay was performed. The silencing of PKC-ε target gene was confirmed by real-time RT-PCR.

3. PKC Assay in Cell-free System

The PKC activity in a cell-free system was quantified by the method described in a publication [Kanno T et al., J Lipid Res 47 (6):1146-1156, 2006]. The summary is as described below.

Synthetic PKC substrate peptide (10 μM) was reacted with various PKC isozymes in a medium containing 20 mM Tris-HCl (pH 7.5), 5 mM Mg-acetate, 10 μM ATP and each DCP-LA optical isomer (10 μM) in the absence of phosphatidylserine and diacylglycerol at 30° C. for 5 min. When the activity with new types of PKC (PKC-δ, -ε, -η and -μ) was to be measured, a medium free of Ca$^{2+}$ was used and when the activity with other PKC isozyme was to be measured, a medium containing 100 μM Ca$^{2+}$ was used. After loading on reversed-phase HPLC (LC-10ATvp, Shimadzu Co., Kyoto, Japan), a substrate peptide peak and a new resultant product peak were detected at the absorbance of 214 nm. The areas of the non-phosphorylated and phosphorylated substrate peptides m were measured (total area corresponds to the concentration of PKC substrate peptide used), and the amount of phosphorylated substrate peptide was calculated. The phosphorylated substrate peptide level (pmol/l min) was used as an index of PKC activity.

(Results)

Figure 2:
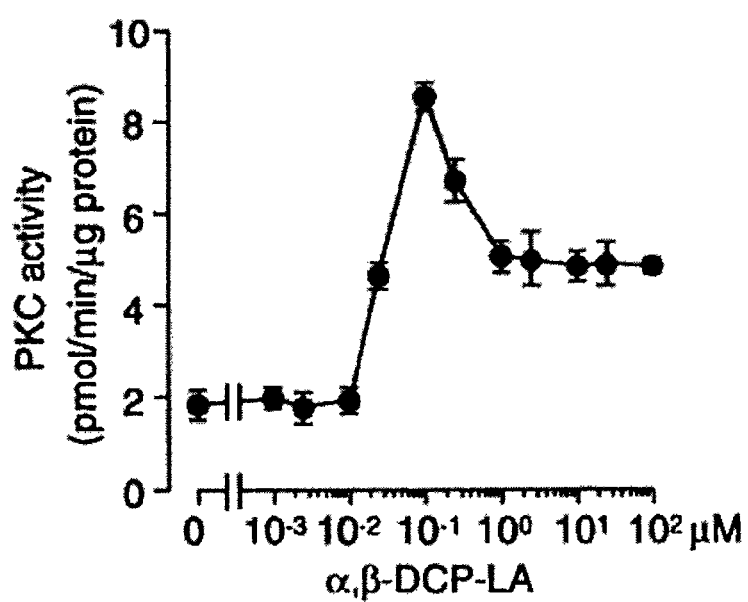
FIG. 2 is a graph showing that the PKC activation action of α,β-DCP-LA on PC-12 cells shows bell-shaped concentration-dependent manner. The PKC activation action at each concentration is shown by the average value (±SEM) (n=6).

The measurement results of the PKC activation action of each DCP-LA optical isomer (concentration used: 100 nM) on PC-12 cells are shown in FIG. 1. The results show that α,β-DCP-LA can activate PKC most strongly in PC-12 cells as compared to the other optical isomers. Furthermore, it was found that the PKC activation action of α,β-DCP-LA shows bell-shaped concentration-dependent manner, and the activation action thereof reaches maximum at about 100 nM (FIG. 2).

Figure 3:
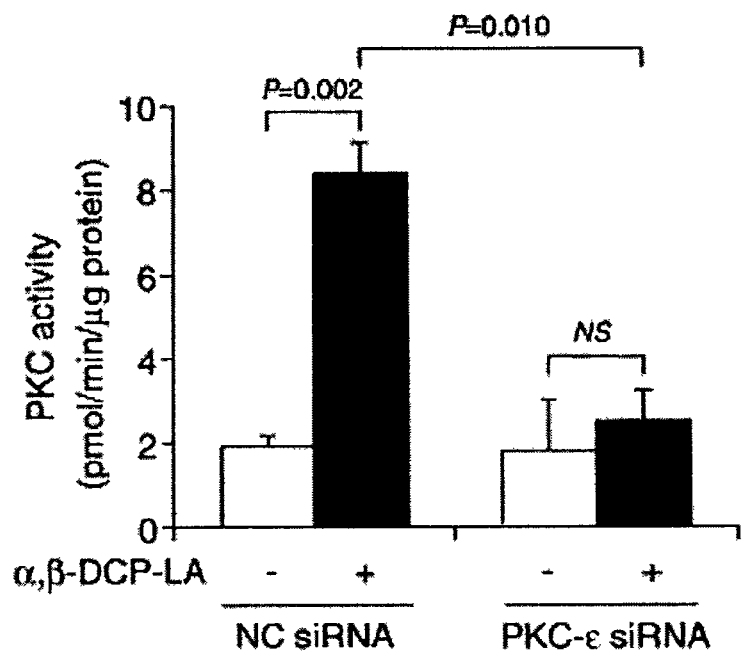
FIG. 3 is a graph showing that α,β-DCP-LA activates PKC-ε on PC-12 cells. The PKC activation action is shown by the average value (±SEM) (n=6). P value; unpaired t-test, NS; no significant difference.
Figure 4:
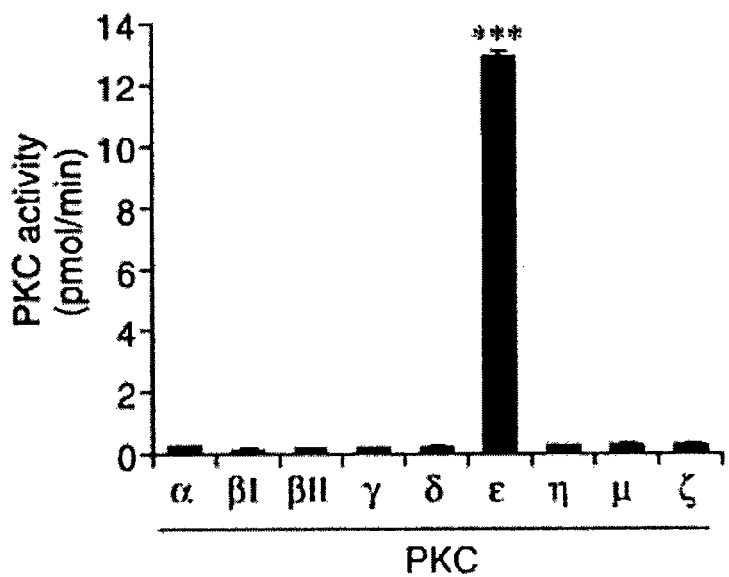
FIG. 4 is a graph showing that α,β-DCP-LA selectively and directly activates PKC-ε. The PKC activation action is shown by the average value (±SEM) (n=6). P<0.001 (comparison with other PKC isozyme); Dunnett's test
Figure 5:
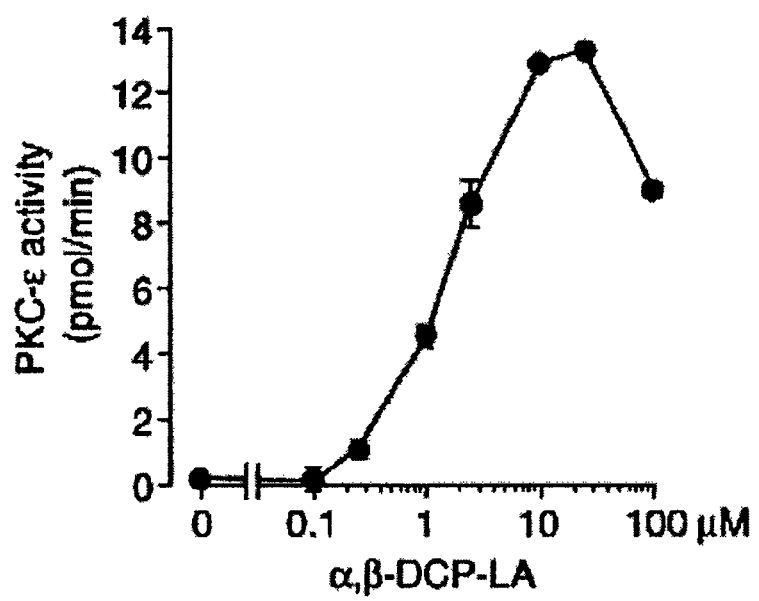
FIG. 5 is a graph showing that the PKC activation action of α,β-DCP-LA in a cell-free system shows bell-shaped concentration-dependent manner. The PKC activation action at each concentration is shown by the average value (±SEM) (n=6).

In addition, the experiment using PKC-ε siRNA showed that PKC activation induced by α,β-DCP-LA is inhibited by knocking down PKC-ε in PC-12 cells (FIG. 3). The results show that α,β-DCP-LA preferentially activates PKC-ε in PC-12 cells. To confirm this, the presence or absence of activation by α,β-DCP-LA was examined by PKC assay using each PKC isozyme in a cell-free system (FIG. 4). The results have confirmed that α,β-DCP-LA induces selective and direct activation of PKC-ε. Moreover, it was found that the PKC activation action of α,β-DCP-LA shows also bell-shaped concentration-dependent manner in a cell-free system as well and the activation action thereof reaches maximum at about 25 μM (FIG. 5).

Figure 6:
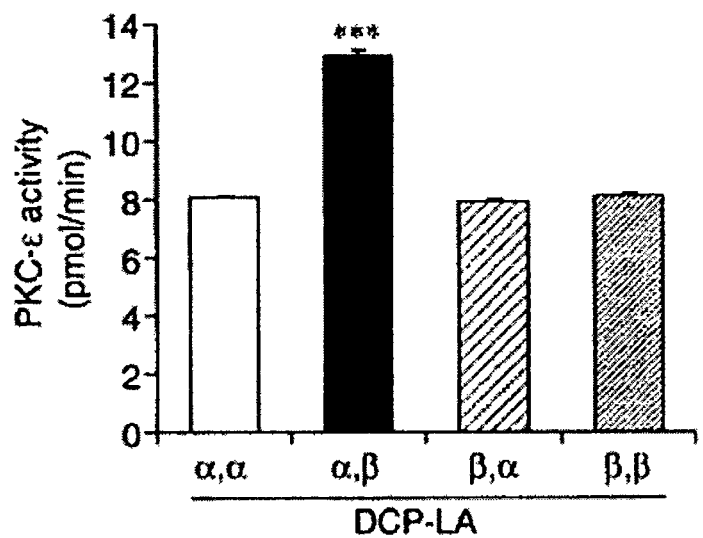
FIG. 6 is a graph showing that, of the 4 kinds of optical isomers, α,β-DCP-LA has the strongest PKC-ε activation action. The PKC-ε activation action is shown by the average value (±SEM) (n=6). *P<0.001 (comparison with PKC-ε activation action induced by α,α-, β,α-, or β,β-DCP-LA); Dunnett's test

Also in the PKC-ε activation action, α,β-DCP-LA showed the highest ability as compared to the other optical isomers (FIG. 6).

From the above results, it was shown that α,β-DCP-LA can selectively and directly activate PKC, particularly PKC-ε, most strongly among the 4 optical isomers.

Experimental Example 2

Figure 7:
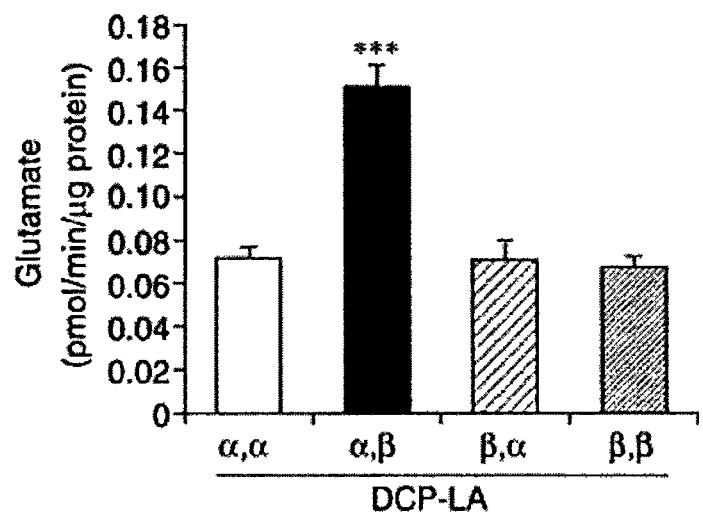
FIG. 7 is a graph showing that, of the 4 kinds of optical isomers, α,β-DCP-LA has the strongest promoting action on glutamic acid release from the hippocampus. The glutamic acid concentration is shown by the average value (±SEM) (n=6). *P<0.001 (comparison with glutamic acid release induced by α,α-, β,α- or β,β-DCP-LA); Dunnett's test
Figure 8:
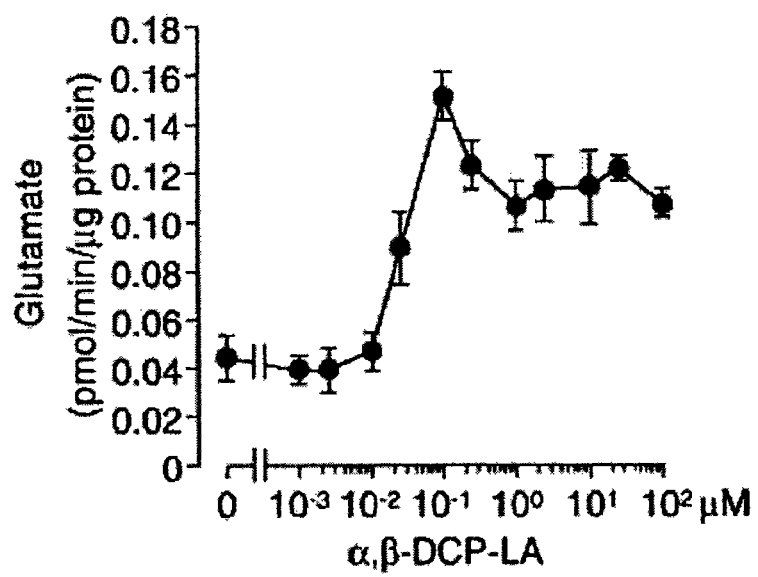
FIG. 8 is a graph showing that the promoting action of α,β-DCP-LA on glutamic acid release from the hippocampus shows bell-shaped concentration-dependent manner. The glutamic acid concentration at each concentration is shown by the average value (±SEM) (n=6).

Among 4 Optical Isomers, α,β-DCP-LA Most Strongly Stimulates Neurotransmitter Release in PKC and α7Ach Receptor-dependent Manner (Material and Method)
Assay of Glutamic Acid, Dopamine and Serotonin Hippocampus, striatum and hypothalamus were isolated from the brain of rat (male Wistar rat, 6-week-old), and 400 μm-thick sections were prepared for each assay of glutamic acid, dopamine and serotonin. The obtained sections were incubated at room temperature for 1 hr, then at 34° C. for 50 min, in a standard artificial cerebrospinal fluid (ACSF) (117 mM NaCl, 3.6 mM KCl, 1.2 mM $NaH_2PO_4$, 1.2 mM $MgCl_2$, 2.5 mM $CaCl_2$, 25 mM $NaHCO_3$, 11.5 mM glucose) oxygenized with 95% $O_2$, 5% $CO_2$. Then, the sections were transferred to a chamber filled with ACSF (1 ml) containing tetrodotoxin (0.5 μM) and oxygenized with 95% $O_2$, 5% $CO_2$, and incubated at 34° C. for 20 min. The incubation was performed in the presence or absence of α,β-DCP-LA, in the presence or absence of nicotine (1 μM), in the presence or absence of DCP-LA optical isomer (100 nM), or in the presence or absence of GF109203X (GF; 100 nM) or α-bungarotoxin (α-BgTX; 100 nM). After incubation, external fluid was recovered and the released glutamic acid was labeled with 4-fluoro-7-nitrobenzofurazan (NBD-F). Then, 20 μ of solution labeled with NBD-F was injected into the column (150× 4.6 mm) and loaded on the HPLC system. Using a fluorescence detector, NBD-F was detected at excitation wavelength 350 nm and luminescence wavelength 450 nm.
(Results)
1. Glutamic Acid Release Stimulation Action The rat hippocampus sections were treated with DCP-LA optical isomer (100 nM) in the presence of nicotine (1 μM), and the released glutamic acid was measured by HPLC. The results are shown in FIG. 7. It was found that α,β-DCP-LA has a remarkably high glutamic acid release stimulation action as compared to the other optical isomers. Moreover, it was found that the glutamic acid release stimulation action of α,β-DCP-LA shows bell-shaped concentration-dependent manner and the stimulation action thereof reaches maximum at about 100 nM (FIG. 8).

Figure 9:
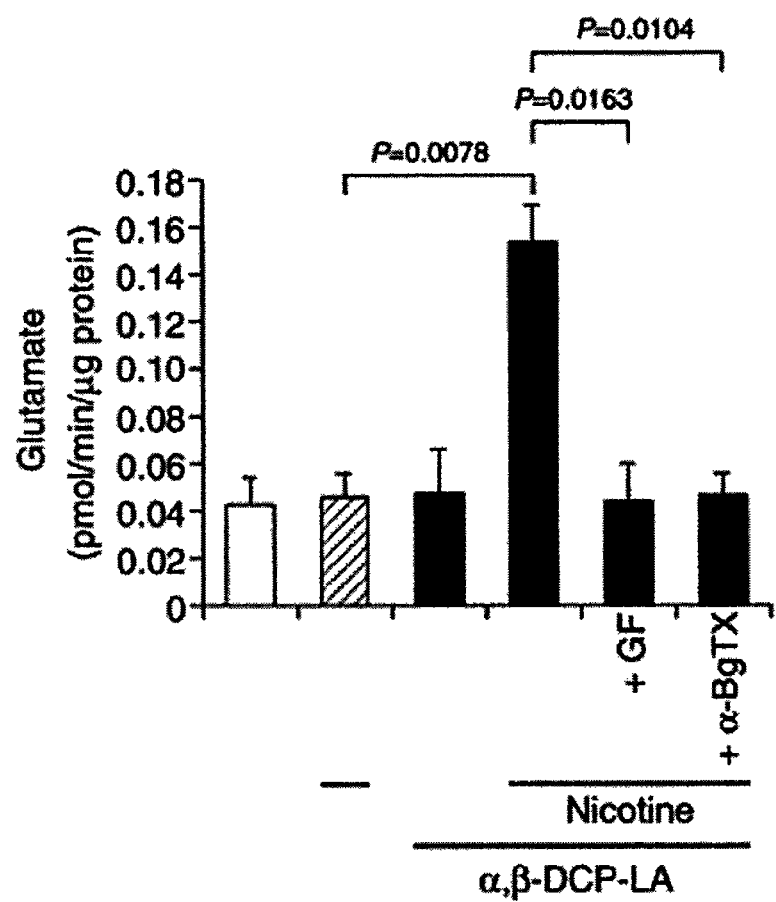
FIG. 9 is a graph showing that α,β-DCP-LA stimulates release of glutamic acid from the hippocampus via interaction of PKC and α7Ac receptor. The glutamic acid concentration is shown by the average value (±SEM) (n=6). P value; unpaired t-test

Whether the stimulation action of α,β-DCP-LA on glutamic acid release from the hippocampus is caused by an interaction of PKC and α7 Ach receptor was examined. The results are shown in FIG. 9. In a non-treated group, a treated group with nicotine alone, and a treated group with α,β-DCP-LA alone did not show a remarkable difference. On the other hand, α,β-DCP-LA remarkably enhanced glutamic acid release caused by nicotine, and the effect thereof was inhibited by GF109203X, which is a PKC inhibitor, and α-BgTX, which is an α7 Ach receptor inhibitor. The results show that α,β-DCP-LA stimulates glutamic acid release from the rat hippocampus in a PKC and α7 Ach receptor-dependent manner.

Figure 10:
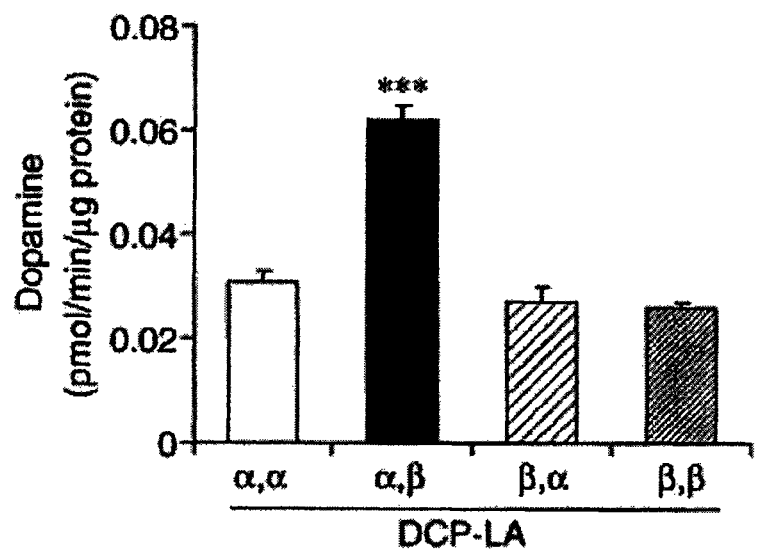
FIG. 10 is a graph showing that, of the 4 kinds of optical isomers, α,β-DCP-LA has the strongest promoting action on dopamine release from the striatum. The dopamine concentration is shown by the average value (±SEM) (n=6). ***P<0.001 (comparison with dopamine release induced by α,α-, β,α- or β,β-DCP-LA); Dunnett's test
Figure 11:
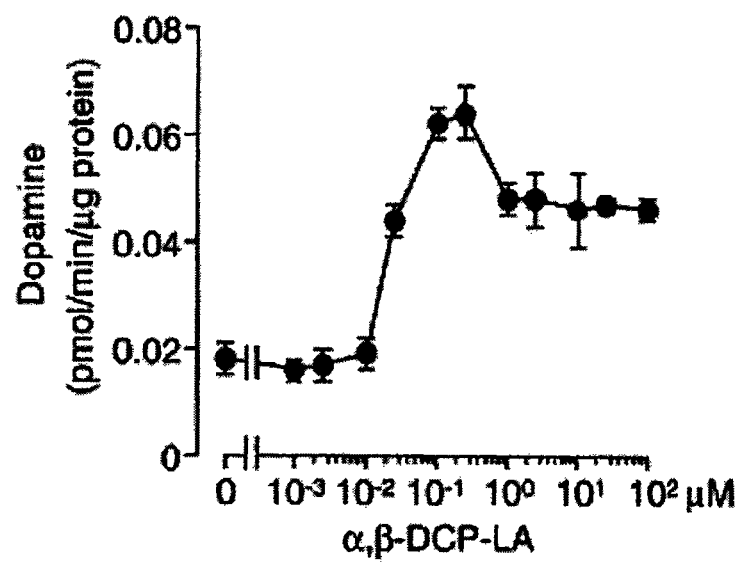
FIG. 11 is a graph showing that the promoting action of α,β-DCP-LA on dopamine release from the striatum shows bell-shaped concentration-dependent manner. The dopamine concentration at each concentration is shown by the average value (±SEM) (n=6).

These results suggest that α,β-DCP-LA stimulates glutamic acid release in the brain and induces LTP (long-term potentiation) to be a cell model of learning and memory, and therefore, can improve various diseases, specifically, age-related cognitive decline, neurodegenerative diseases (Alzheimer's disease, Parkinson's disease, diffuse Lewy body diseases (dementia having Lewy body), frontotemporal dementia, Pick's disease, Creutzfeldt-Jakob disease, Huntington's disease, progressive supranuclear palsy etc.), vascular dementia (multiple lacunar infarcts, Binswanger's disease and diffuse infarction in the white matter etc.), viral encephalitis (herpes encephalitis, HIV encephalitis (dementia due to AIDS) and syphilitic encephalitis etc.), alcohol-induced persisting dementia (Korsakoff's syndrome and Wernicke encephalopathy etc.), and cognitive decline caused by other diseases (cognitive decline due to normal pressure hydrocephalus, chronic subdural hematoma, moya-moya disease, dementia pugilistica, hypothyroidism, hypercalcemia, hypoglycemia, vitamin B1 deficiency, vitamin B 12 deficiency and folic acid deficiency and the like) and the like.
2. Dopamine Release Stimulation Action The rat striatum sections were treated with DCP-LA optical isomer (100 nM) in the presence of nicotine (1 μM), and the released dopamine was measured by HPLC. The results are shown in FIG. 10. It was found that α,β-DCP-LA has a remarkably high dopamine release stimulation action as compared to the other optical isomers. Moreover, it was found that the dopamine release stimulation action of α,β-DCP-LA shows bell-shaped concentration-dependent manner and the stimulation action thereof reaches maximum at about 250 nM (FIG. 11).

Figure 12:
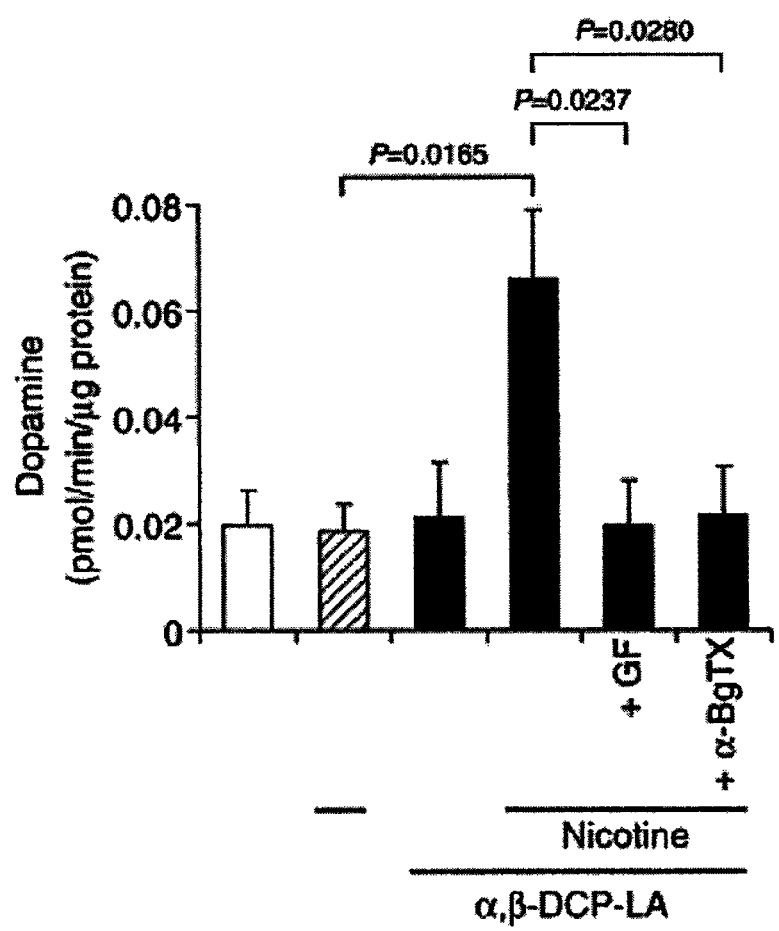
FIG. 12 is a graph showing that α,β-DCP-LA stimulates release of dopamine from the striatum via interaction of PKC and α7Ac receptor. The dopamine concentration is shown by the average value (±SEM) (n=6). P value; unpaired t-test

Whether the stimulation action of α,β-DCP-LA on dopamine release from the striatum is caused by an interaction of PKC and α7 Ach receptor was examined. The results are shown in FIG. 12. In a non-treated group, a treated group with nicotine alone, and a treated group with α,β-DCP-LA alone did not show a remarkable difference. On the other hand, α,β-DCP-LA remarkably enhanced dopamine release caused by nicotine, and the effect thereof was inhibited by GF109203X, which is a PKC inhibitor, and α-BgTX, which is an α7 Ach receptor inhibitor. The results show that α,β-DCP-LA stimulates dopamine release from the rat striatum in a PKC and α7 Ach receptor-dependent manner.

Figure 13:
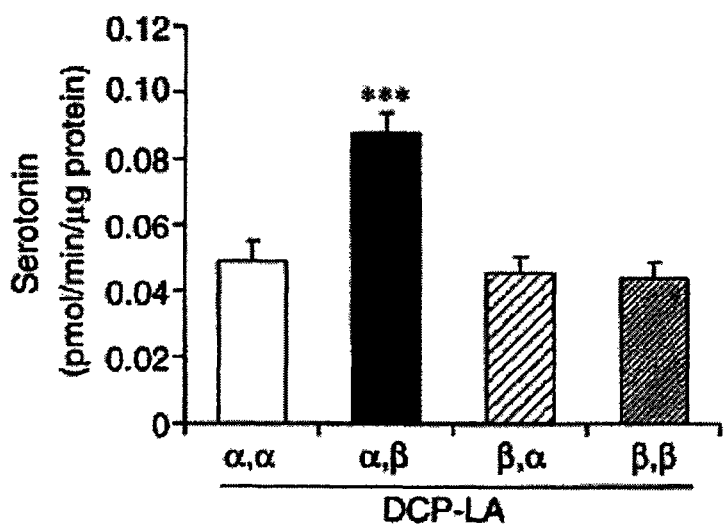
FIG. 13 is a graph showing that, of the 4 kinds of optical isomers, α,β-DCP-LA has the strongest promoting action on serotonin release from the hypothalamus. The serotonin concentration is shown by the average value (±SEM) (n=6). ***P<0.001 (comparison with serotonin release induced by α,α-, β,α- or β,β-DCP-LA); Dunnett's test
Figure 14:
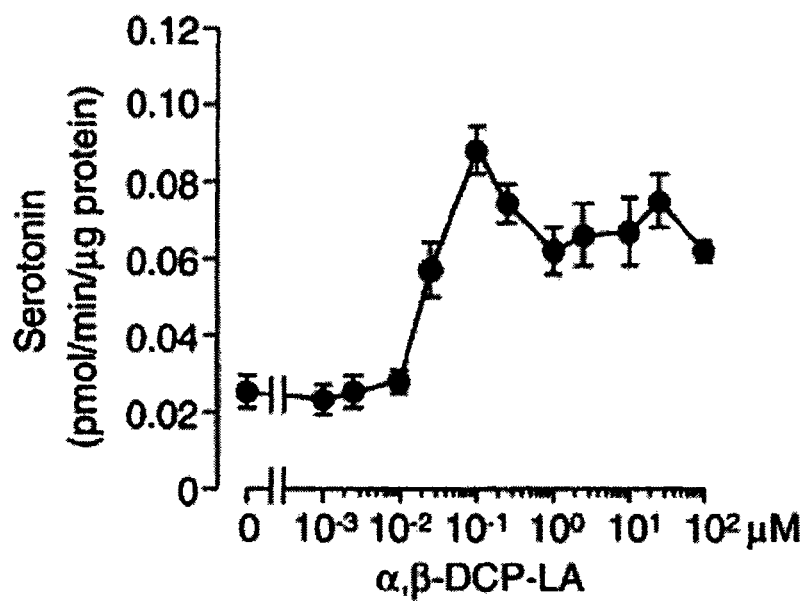
FIG. 14 is a graph showing that the promoting action of α,β-DCP-LA on serotonin release from the hypothalamus shows bell-shaped concentration-dependent manner. The serotonin concentration at each concentration is shown by the average value (±SEM) (n=6).

These results suggest that α,β-DCP-LA stimulates dopamine release in the brain and can improve Parkinson's disease, diffuse Lewy body disease (dementia having Lewy body) and extrapyramidal disease, which are caused by a decrease or lack of dopamine.
3. Serotonin Release Stimulation Action The rat hypothalamus sections were treated with DCP-LA optical isomer (100 nM) in the presence of nicotine (1 μM), and the released serotonin was measured by HPLC. The results are shown in FIG. 13. It was found that α,β-DCP-LA has a remarkably high serotonin release stimulation action as compared to the other optical isomers. Moreover, it was found that the serotonin release stimulation action of α,β-DCP-LA shows bell-shaped concentration-dependent manner and the stimulation action thereof reaches maximum at about 100 nM (FIG. 14).

Figure 15:
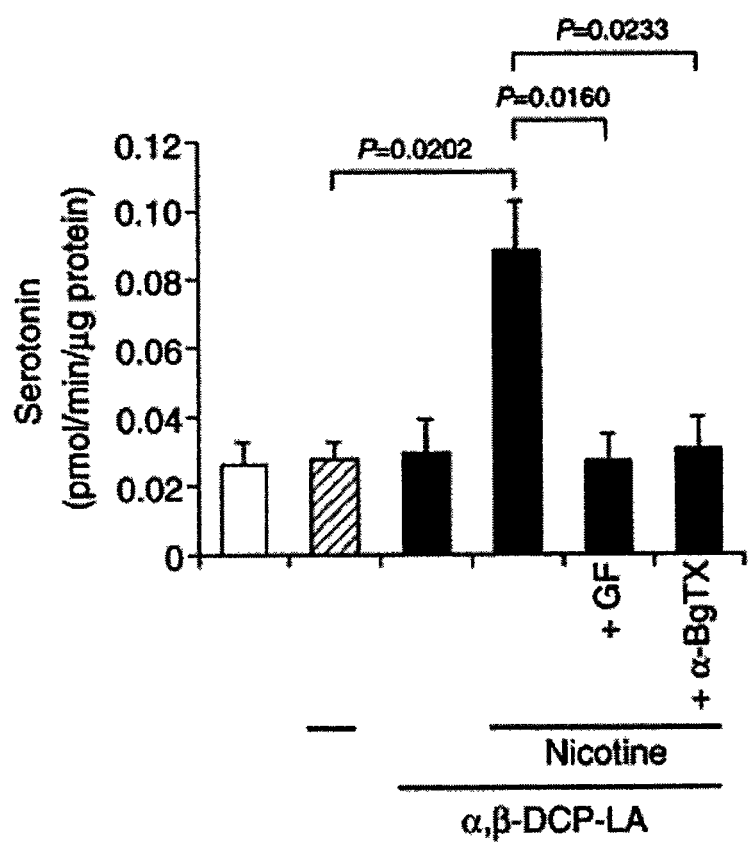
FIG. 15 is a graph showing that α,β-DCP-LA stimulates release of serotonin from the hypothalamus via interaction of PKC and α7Ac receptor. The serotonin concentration is shown by the average value (±SEM) (n=6). P value; unpaired t-test

Whether the stimulation action of α,β-DCP-LA on serotonin release from the hypothalamus is caused by an interaction of PKC and α7 Ach receptor was examined. The results are shown in FIG. 15. In a non-treated group, a treated group with nicotine alone, and a treated group with α,β-DCP-LA alone did not show a remarkable difference. On the other hand, α,β-DCP-LA remarkably enhanced serotonin release caused by nicotine, and the effect thereof was inhibited by GF109203X, which is a PKC inhibitor, and α-BgTX, which is an α7 Ach receptor inhibitor. The results show that α,β-DCP-LA stimulates serotonin release from the rat hypothalamus in a PKC and α7 Ach receptor-dependent manner.

These results suggest that α,β-DCP-LA stimulates serotonin release in the brain and/or peripheral nerve and can improve panic disorder, sleep disorder, emotional disturbance syndrome, frustrated disease, pain and gastrointestinal motility disorder and the like.

Experimental Example 3

Among 4 Optical Isomers, α,β-DCP-LA can be Expected to Provide Highest Learning Dysfunction Improving Effect (Material and Method)

Using senescence-accelerated mouse (accelerated-senescence-prone mice 8: SAMP8) and normal senescence mouse (accelerated-senescence-resistant mice 1: SAMR1) as a control thereof, a water maze test was performed. Male SAMP8 and SAMR1 (22- to 25-week-old) were available from Takeda Pharmaceutical Company Limited (Osaka, Japan). The mice were individually raised in a cage at 23±1° C., 12 hr light/dark cycle (lighted at 7:00 am), and allowed to freely ingest feed (solid feed) and water.

Racemate DCP-LA and 4 optical isomers DCP-LA (α,α-, α,β-, β,α-, β,β-DCP-LA), each dissolved in 0.1 ml polyethylene glycol (PEG), or 0.1 ml PEG were orally administered once a day from the day when the water maze test was started. For each group, the water maze test was performed twice a day for 8 days, and the time required to reach a platform (acquisition latency) was measured.

For the water maze test, a circular plastic water tank (diameter 90 cm, depth 36 cm) was used. The inside of the water tank was completely painted in black, and dark water with India ink was filled up to 20 cm from the bottom (22° C.). A platform (diameter 11 cm) painted in black was placed in water such that it was 1 cm below the water surface. The water tank was placed in a test room, and several marks seen by the mice from the water tank were put thereon. During the test, the position of the marks was not changed. A platform was placed a predetermined position from the equal distance from the center and the end of the water tank, namely, center of one quadrant. At one of the randomly selected 5 points, the mouse was released facing the wall of the water tank, and the time necessary for evacuating on the platform (acquisition latency) was measured. When smoothly evacuated, the mouse was left on the platform for 10 seconds. From the day of water maze test and during the test, polyethylene glycol (PEG) alone or racemate DCP-LA (1 mg/kg), α,α-DCP-LA (0.25 mg/kg), α,β-DCP-LA (0.25 mg/kg), β,α-DCP-LA (0.25 mg/kg), or β,β-DCP-LA (0.25 mg/kg), each dissolved in PEG, was orally administered every day. The water maze test was performed twice a day, and the second test was started at 2 min from the first test. The test was continuously performed for 8 days, and the average value (±SEM) of acquisition latency of continuous 2 days until the mouse reached the platform was calculated (each n=5).

(Results)

Figure 16:
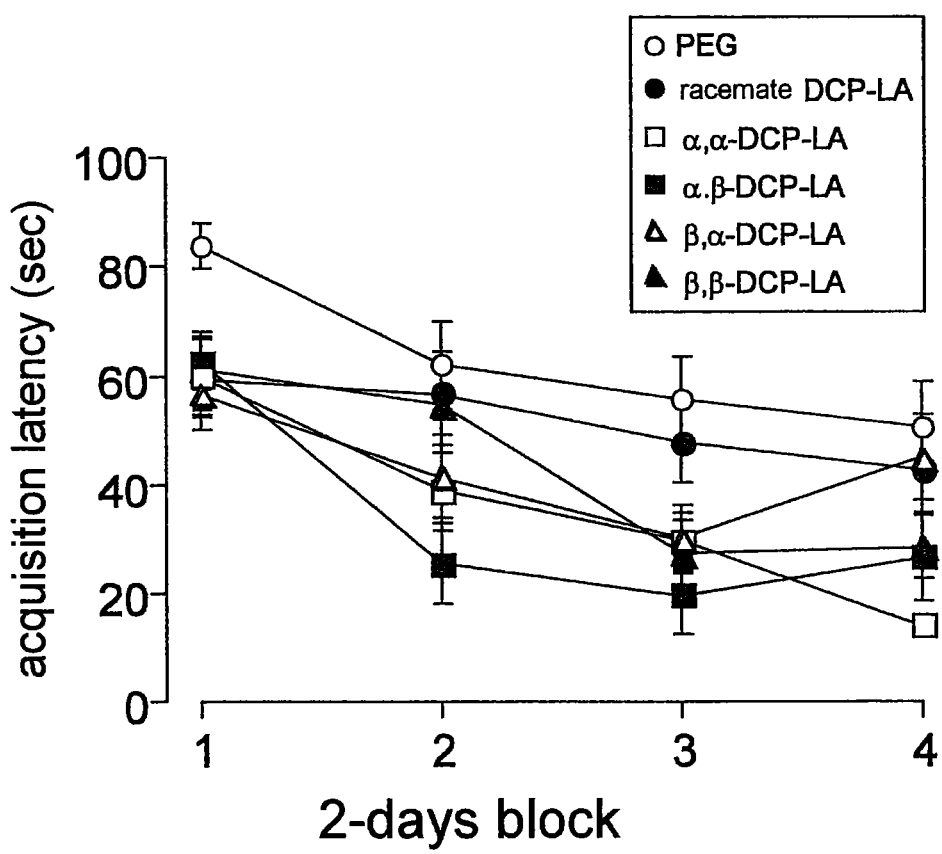
FIG. 16 shows the effect of α,β-DCP-LA for spatial learning disorder associated with aging. The results of a water maze test using senescence-accelerated mouse and normal senescence mouse as a control thereof are shown. The racemate and 4 optical isomers (α,α-, α,β-, β,α-, β,β-DCP-LA) were examined (Fisher's PLSD test).

The acquisition latency of SAMP8 administered with PEG was significantly extended as compared to that of SAMR1 administered with PEG (P=0.0084, Fisher's PLSD test). The results mean decreased learning function due to the aging of SAMP8. Racemate DCP-LA (1 mg/kg), α,α-DCP-LA (0.25 mg/kg), α,β-DCP-LA (0.25 mg/kg), β,α-DCP-LA (0.25 mg/kg), and β,β-DCP-LA (0.25 mg/kg) administration groups all showed shortened acquisition latency, which was extended significantly, as compared to the PEG administration group (as compared to PEG administration group: racemate DCP-LA administration group P=0.0248; α,α-DCP-LA administration group P<0.0001; α,β-DCP-LA administration group P<0.0001; β,α-DCP-LA administration group P=0.0001; β,β-DCP-LA administration group P<0.0001, Fisher's PLSD test) (FIG. 16). The α,α-DCP-LA (0.25 mg/kg) administration group and the α,β-DCP-LA (0.25 mg/kg) administration group showed significantly shortened acquisition latency as compared to the racemate DCP-LA (1 mg/kg) administration group (as compared to racemate DCP-LA administration group: α,α-DCP-LA administration group P=0.0016; α,β-DCP-LA administration group P=0.0007, Fisher's PLSD test) (FIG. 16). Furthermore, α,β-DCP-LA (0.25 mg/kg) administration group showed significantly shortened acquisition latency as compared to the α,α-DCP-LA (0.25 mg/kg) administration group (as compared to α,α-DCP-LA administration group: α,β-DCP-LA administration group P=0.0023, Fisher's PLSD test) (FIG. 16). The above results show that racemate DCP-LA and all the 4 optical isomers DCP-LA have an action to improve decreased learning function due to the aging, and particularly, α,β-DCP-LA is expected to show the highest improving effect for decreased learning function due to the aging.

[Sequence Listing Free Text]

SEQ ID NO: 1: synthetic PKC substrate peptide
SEQ ID NO: 2: siRNA
SEQ ID NO: 3: siRNA Industrial Applicability The agent containing α,β-DCP-LA as an active ingredient of the present invention has a selectively strong selective PKC-ε activation action, and further, can stimulate release of neurotransmitters such as glutamic acid, dopamine and serotonin.

Therefore, it controls the balance of the neural activity of the whole brain and is useful for the treatment of various neuropsychiatric diseases such as dementia, Parkinson's disease, depression and the like.

This application is based on a patent application No. 2010-255967 (filing date: Nov. 16, 2010) filed in Japan, the contents of which are incorporated in full herein. In addition, the contents disclosed in any publication cited in the present specification, including patents and patent applications, are hereby incorporated in their entireties by reference, to the extent that they have been disclosed herein.

The invention claimed is:

1. A compound represented by the following formula:

or a pharmaceutically acceptable salt thereof.

2. A selective PKC-ε activator containing the compound according to claim 1 or a pharmaceutically acceptable salt thereof as an active ingredient.

3. A therapeutic agent for a neurotransmitter release disorder, containing the compound according to claim 1 or a pharmaceutically acceptable salt thereof as an active ingredient.

4. A therapeutic agent for a neuropsychiatric disease, containing the compound according to claim 1 or a pharmaceutically acceptable salt thereof as an active ingredient.

5. The agent according to claim 4, wherein the neuropsychiatric disease is at least one kind selected from the group consisting of an age-related cognitive decline, neurodegenerative disease, vascular dementia, viral encephalitis, alcohol-induced persisting dementia, and cognitive decline caused by other disease, Parkinson's disease, extrapyramidal disease, depression, panic syndrome, emotional disturbance syndrome, and frustrated disease.

6. The agent according to claim 5, wherein the neurodegenerative disease is Alzheimer's disease, Parkinson's disease, dementia having Lewy body frontotemporal dementia, Pick's disease, Creutzfeldt-Jakob disease, Huntington's disease, or progressive supranuclear palsy.

7. The agent according to claim 5, wherein the vascular dementia is caused by multiple lacunar infarcts, Binswanger's disease, or diffuse infarction in the white matter.

8. The agent according to claim 5, wherein the viral encephalitis is herpes encephalitis, HIV encephalitis or syphilitic encephalitis.

9. The agent according to claim 5, wherein the alcohol-induced persisting dementia is Korsakoff's syndrome or Wernicke encephalopathy.

10. The agent according to claim 5, wherein the cognitive decline caused by other disease is caused by normal pressure hydrocephalus, chronic subdural hematoma, moya-moya disease, dementia pugilistica, hypothyroidism, hypercalcemia, hypoglycemia, vitamin B1 deficiency, vitamin B12 deficiency, or folic acid deficiency.

11. A therapeutic agent for insomnia, pain or gastrointestinal motility disorder, containing the compound according to claim 1 or a pharmaceutically acceptable salt thereof as an active ingredient.

12. A method for the treatment of a neuropsychiatric disease, comprising administering an effective amount of the compound according to claim 1 or a pharmaceutically acceptable salt thereof to a subject.

13. A method for the treatment of insomnia, pain or a gastrointestinal motility disorder, comprising administering an effective amount of the compound according to claim 1 or a pharmaceutically acceptable salt thereof to a subject.

14. A compound represented by the following formula:

or a pharmaceutically acceptable salt thereof, which is used for the treatment of at least one kind of a disease or pathology selected from a neuropsychiatric disease, insomnia, pain and a gastrointestinal motility disorder.

* * * * *

SEQUENCE LISTING

```
<160> NUMBER OF SEQ ID NOS: 3

<210> SEQ ID NO 1
<211> LENGTH: 10
<212> TYPE: PRT
<213> ORGANISM: Artificial
<220> FEATURE:
<223> OTHER INFORMATION: PKC substrate synthetic peptide
```

```
<220> FEATURE:
<221> NAME/KEY: MOD_RES
<222> LOCATION: (1)..(1)
<223> OTHER INFORMATION: Pyr-Lys; Pyr is pyruvic acid

<400> SEQUENCE: 1

Xaa Arg Pro Ser Gln Arg Ser Lys Tyr Leu
1               5                   10

<210> SEQ ID NO 2
<211> LENGTH: 22
<212> TYPE: DNA
<213> ORGANISM: Artificial
<220> FEATURE:
<223> OTHER INFORMATION: siRNA

<400> SEQUENCE: 2
cacaucagug acgaacucau tt                                              22

<210> SEQ ID NO 3
<211> LENGTH: 22
<212> TYPE: DNA
<213> ORGANISM: Artificial
<220> FEATURE:
<223> OTHER INFORMATION: siRNA

<400> SEQUENCE: 3
augaguucgu cacugaugug tt                                              22
```